US007695936B2

(12) United States Patent
Carter et al.

(10) Patent No.: US 7,695,936 B2
(45) Date of Patent: Apr. 13, 2010

(54) KNOBS AND HOLES HETEROMERIC POLYPEPTIDES

(75) Inventors: Paul J. Carter, San Francisco, CA (US); Leonard G. Presta, San Francisco, CA (US); John B. Ridgway, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 661 days.

(21) Appl. No.: 11/533,709

(22) Filed: Sep. 20, 2006

(65) Prior Publication Data

US 2007/0014794 A1 Jan. 18, 2007

Related U.S. Application Data

(63) Continuation of application No. 10/010,245, filed on Dec. 7, 2001, which is a continuation of application No. 08/974,183, filed on Nov. 19, 1997, now abandoned, which is a continuation of application No. 08/399,106, filed on Mar. 1, 1995, now Pat. No. 5,731,168.

(51) Int. Cl.
| | |
|---|---|
| C07K 16/00 | (2006.01) |
| C07K 16/46 | (2006.01) |
| C07K 19/00 | (2006.01) |
| C07K 14/00 | (2006.01) |
| A61K 39/395 | (2006.01) |
| C12N 5/10 | (2006.01) |

(52) U.S. Cl. .................... 435/69.1; 435/69.7; 435/70.1; 435/71.1; 435/325; 530/350; 530/387.1; 530/387.3; 530/300; 424/130.1; 424/133.1; 424/136.1; 424/178.1

(58) Field of Classification Search ........................ None
See application file for complete search history.

(56) References Cited

U.S. PATENT DOCUMENTS 5,821,333 A 10/1998 Carter et al.

FOREIGN PATENT DOCUMENTS

WO WO 92/10209 6/1992
WO WO 93/11162 6/1993

OTHER PUBLICATIONS

Norel et al., Biopolymers, vol. 34, 1994, pp. 933-940.*
Ashkenazie et al., "Immunoadhesins" *Intern. Rev. Immunol.* 10:219-227 (1993).
Belshaw et al., "Rational Design of Orthogonal Receptor-Ligand Combinations" *Angew. Chem. Int. Ed. Engl.* 34(19):2129-2132 (1995).
Berg et al., "Bispecific Antibodies that Mediate Killing of Cells Infected with Human Immunodeficiency Virus of Any Strain" *Proc. Natl. Acad. Sci. USA* 88:4723-4727 (Jun. 1991).

Brennan et al., "Preparation of bispecific antibodies by chemical recombination of monoclonal immunoglobulin $G_1$ fragments" *Science* 229:81-83 (Jul. 5, 1985).
Chamow et al., "A Humanized, Bispecific Immunoadhesin-Antibody That Retargets CD3+ Effectors to Kill HIV-1-Infected Cells" *Journal of Immunology* 153(9);4268-4280 (Nov. 1, 1994).
Crick, "Is α-Keratin a Coiled Coil?" *Nature* (letter to editor) 170:882-883 (1952).
Crick, "The Packing of α-Helices: Simple Coiled-Coils" *Acta Crystallographica* 6(8-9):689-697 (1953).
Dietsch et al., "Bispecific Receptor Globulins, Novel Tools for the Study of Cellular Interactions" *Journal of Immunological Methods* 162:123-132 (1993).
Ellerson et al., "Isolation and Characterization of a Fragment Corresponding to the $C_\gamma$ Homology Region of Human Immunoglobin $G^1$." *Journal of Immunology* 116(2):510-517 (Feb. 1976).
Fanger et al., "Bispecific Antibodies" *Critical Reviews in Immunology* 12(3,4):101-124 (1992).
Gruber et al., "Efficient Tumor Cell Lysis Mediacted by a Bispecific Single Chain Antibody Expressed in *Escherichia coli*" *Journal of Immunology* 152:5368-5374 (1994).
Hollenbaugh et al., "Interaction of P-Selectin (CD62) and Its Cellular Ligand: Analysis of Critical Residues" *Biochemistry* 32:2960-2966 (1993).
Holliger et al., "'Diabodies': Small Bivalent and Bispecific Antibody Fragments" *Proc. Natl. Acad. Sci. USA* 90:6444-6448 (Jul. 1993).
John et al., "Two Pairs of Oppositely Charged Amino Acids from Jun and Fos Confer Heterodimerization to GCN4 Leucine Zipper" *Journal of Biological Chemistry* 269(23):16247-16253 (1994).
Julia et al, "Rat liver alcohol dehydrogenase of class III" *European Journal of Biochemistry* 172:73-83 (1988).
Landschulz et al., "The Leucine Zipper: A Hypothetical Structure Common to a New Class of DNA Binding Proteins." *Science* . 240:1759-1764 (Jun. 1988).
Landschulz, "The Leucine Zipper:A Hypothetical Structure Common to a New Class of DNA Binding Proteins" *Science* 240:1760-1764 (Jun. 1988).

(Continued)

*Primary Examiner*—Jeffrey Stucker
*Assistant Examiner*—Stephen Gucker
(74) *Attorney, Agent, or Firm*—Jones Day

(57) ABSTRACT

The invention relates to a method of preparing heteromultimeric polypeptides such as bispecific antibodies, bispecific immunoadhesins and antibody-immunoadhesin chimeras. The invention also relates to the heteromultimers prepared using the method. Generally, the method involves introducing a protuberance at the interface of a first polypeptide and a corresponding cavity in the interface of a second polypeptide, such that the protuberance can be positioned in the cavity so as to promote heteromultimer formation and hinder homomultimer formation. "Protuberances" are constructed by replacing small amino acid side chains from the interface of the first polypeptide with larger side chains (e.g. tyrosine or tryptophan). Compensatory "cavities" of identical or similar size to the protuberances are created in the interface of the second polypeptide by replacing large amino acid side chains with smaller ones (e.g. alanine or threonine). The protuberance and cavity can be made by synthetic means such as altering the nucleic acid encoding the polypeptides or by peptide synthesis.

73 Claims, 11 Drawing Sheets

OTHER PUBLICATIONS

Marcote et al., "A Three-Dimensional Model of the Cdc2 Protein Kinase:Localization of Cyclin- and Sucl-Binding Regions and Phosphorylation Sites" *Molecular & Cellular Biology* 13(8):5122-5131 (Aug. 1993).

McPhee et al., "Engineering Human Immunodeficiency Virus 1 Protease Heterodimers as Macromolecular Inhibitors of Viral Maturation" *Proc. Natl. Acad. Sci.* 93:11477-11481 (1996).

Milstein and Cuello, "Hybrid Hybridomas and Their Use in Immunohistochemistry" *Nature* 305:537-540 (Oct. 6, 1983).

Nolan et al., "Bifunctional antibodies: concept, production and applications" *Biochimica et Biophysica Acta* 1040:1-11 (1990).

O'Shea et al., "Mechanism of Specificity in the Fos-Jun Oncoprotein Heterodimer" *Cell* 68:699-708 (1992).

O'Shea et al., "Peptide 'Velcro*' : Design of a Heterodimeric Coiled Coil" *Current Biology* 3(10):658-667 (1993).

Presta et al., "The Binding Site on Human Immunoglobulin E for Its High Affinity Receptor" *Journal of Biological Chemistry* 269(42):26368-26373 (Oct. 21, 1994).

Ridgway et al., "'Knobs-into-holes' Engineering of Antibody $C_H3$ Domains for Heavy Chain Heterodimerization" *Protein Engineering* 9(7):617-621 (1996).

Rodrigues et al., "Engineering Fab' Fragments for Efficient $F(ab)_2$ Formation in *Escherichia coli* and for Improved In Vivo Stability" *The Journal of Immunology* 151(12):6954-6961 (Dec. 15, 1993).

Roit et al. *Immunology*, 3rd edition, Mosby Limited pp. 4.8 (1993).

Roitt et al., "Antigen Receptor Molecules" *Immunology*, Mosby Limited, 3rd edition pp. 4.8 (1996).

Sawa et al., "Functional domains of transcription factor hGABPβ1/E4TF1-53 required for nuclear localization and transcription activation" *Nucleic Acids Research* 24(24):4954-4961 (1996).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217-225 (Jan. 1, 1992).

Songsivilai et al., "Bispecific antibody: a tool for diagnosis and treatment of disease" *Clin. Exp. Immunol.* 79:315-321 (1990).

Tso et al., "Preparation of a Bispecific F(ab') /sub2/nor Targeted to the Human IL-2 Receptor" *Journal of Hematotherapy* 4:389-394 (1995).

Vinson et al., "Dimerization Specificity of the Leucine Zipper-Containing bZIP Motif on DNA Binding: Prediction and Rational Design" *Genes & Development* 7:1047-1058 (1993).

Ward et al., "Effects of Engineering Complementary Charged Residues into the Hydrophobic Subunit Interface of Tyrosyl-tRNA Synthetase" *Biochemistry* 26(13):4131-4138 (1987).

Zhu et al., "Remodeling Domain Interfaces to Enhance Heterodimer Formation" (In Press) pp. 1-31 (1997).

Kostelny et al., "Formation of a Bispecific Antibody by the Use of Leucine Zippers" *Journal of Immunology* 148(5):1547-1553 (Mar. 1, 1992).

Zhang, X.K., et al., "Mutations that Alter Ligand-Induced Switches and Dimerization Activities in the Retinoid X Receptor", Molecular and Cellular Biology, vol. 14, No. 6, pp. 4311-4323, (Jun. 1994).

Goodman, E.M., et al., "Periodicity of Amide Proton Exchange Rages in a Coiled-Coil Leucine Zipper Peptide", Biochemistry, 30, pp. 11615-11620, (1991).

Jefferis, R., et al., "*IgG-Fc-mediated effector functions: molecular definition of interaction sites for effector ligands and the role of glycosylation*", Immunol. Rev.: 163:59-76, (Jun. 1998)—PubMed Abstract.

Thies, M.J., , et al., "*Folding and association of the antibody domain CH3: prolyl isomerization preceeds dimerization*", J. Mol. Biol.: 293(1):67-79, (Oct. 15, 1999)—PubMed Abstract.

* cited by examiner

Monospecific Bivalent    Bispecific Monovalent
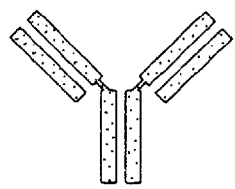 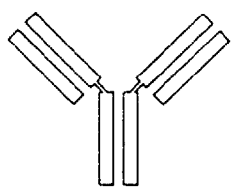
Monospecific Monovalent
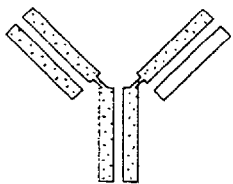 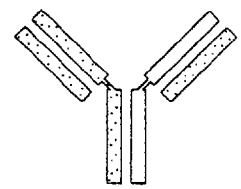 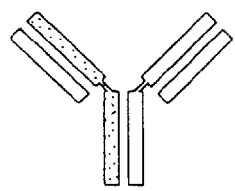 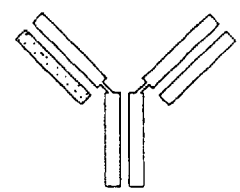
"Inactive"
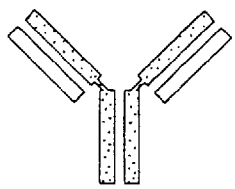 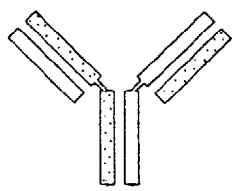 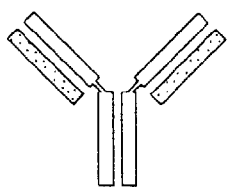
FIG. 1

BsF(ab')2
CHEMICALLY COUPLED
RODENT FRAGMENTS

BsF(ab')2
CHEMICALLY COUPLED
E. coli DERIVED FRAGMENTS

BsF(ab')2
LEUCINE ZIPPER
ASSEMBLED fos  jun sFv DIMER

DIABODY

```
              edge,interface
              -----------
            B i B I B I     B i
IgG    G Q P R E P Q V Y T L P P S R E E M T K N Q
IgA    G N T F R P Q V H L L P P P S E ELA L B Z L
IgD    Q A P V K L S L N L L A S S D P - - P E A A
IgE    G P R A A P E V Y A F A T P E W P G S R D K
IgM    - D Z B T A I R V F A I P P S F ASIFL T K S
                         350             360 middle,interface              exterior
        ---------------              -----------
       B I B I B I B i             B   B   B
IgG    V S L T C L V K G F Y P S D I A V E W E S N
IgA    V T L T C L A R G F S P K D V L V R W L Q G
IgD    S W L L C E V S G F S P P N I L L M W L EDQ
IgE    R T L A C L I Q N F M P E D I S V Q W L H N
IgM    T K L T C L V T D L T T Y BSV T I S W T R Z
                   370              380 edge,interface
                    --------------------
                    I       i       I
IgG    D - G Q P E N N Y K T T P P V/M L D S D G S
IgA    S Q E L P R E K Y L T W A S R     Q Z PSQGTTT
IgD    R E V N T S G F A P A R P P P     Q P G S T T
IgE    E V Q L P D A R H S T T Q P R     K T K G S G
IgM    D - - G E A V K T H T B I S Z     S H P B A T
                     390              400 middle,interface                    exterior
         --------------------              ---------------
        B I B I B I   B i B           B        B   B   B
IgG    F F L Y S K/R L T V D K S R W Q Q G N V F S C S V M
IgA    F A V T S I   L R V A A E D W K K G D T F S C M V G
IgD    F W A W S V   L R V P A P P S P Q P A T Y T C V V S
IgE    F F V F S R   L E V T R A E W E Q K D E F I C R A V
IgM    F S A V G E   A S I C E B B W B S G E R F T C T V T
                  410                420 exterior
                  -------------
       B           b     b     b
IgG    H E A L H N H Y T Q K S L S L S P G K
IgA    H E A L P L A F T Q K T I D R L A G K
IgD    H E D - S R T L L N A S R S L E V S Y
IgE    H E A ASP S Q T V Q R A V S V N P G K
IgM    H T D L P S P L K Q T I S R P K - - -
       430              440
```

FIG. 5

```
                    EDGE                    MIDDLE
        361                  370              ↓390
hIgG1   G - Q P R E P Q V Y T L P P S R E E - - M T K N Q V S L T C
hIgG2   G - Q P R E P Q V Y T L P P S R E E - - M T K N Q V S L T C
hIgG3   G - Q P R E P Q V Y T L P P S R E E - - M T K N Q V S L T C
hIgG4   G - Q P R E P Q V Y T L P P S Q E E - - M T K N Q V S L T C 361                  370              390
mIgG1   G - R P K A P Q V Y T I P P P K E Q - - M A K D K V S L T C
mIgG2A  G - P P V R A P Q V Y V L P P P A E E - - M T K K N Z F S L T C
mIgG2B  G - L V R A P Q V Y V L P P P A E Q - - L S R K D V S L T C
mIgG3   G - R A Q T P Q V Y T I P P P R E Q - - M S K K K V S L T C 400                  410
hIgG1   L V K G F Y P S D - I A V E W E S - B D - G Z P Z B N Y K
hIgG2   L V K G F Y P S D - I A V E W E S - N G - Q P E N N Y K
hIgG3   L V K G F Y P S D - I A V E W E S - S G - Q P E N N Y N
hIgG4   L V K G F Y P S D - I A V E W Z S - N G - Q P E N N Y K mIgG1   M I T D F F P E D I T V - E W Q W - - B G - Q P A E N Y K
mIgG2A  M I T G F L P A E I H V - E W T S - - N G - R T E Q N Y K
mIgG2B  L V V G F N P G D I S V - E W T N - - N G - H T E E N Y K
mIgG3   L V T N F F S E A I S V - E W E R - - N G - E L E Q D Y K
```

FIG.6A

```
                    EDGE              MIDDLE                  450
hIgG1        → T T P P V L D S -- -- -- -- G S F F L Y S K L T V D K S R W Q Q
hIgG2        → T T P P M L D D S -- -- -- G S F F L Y S K L T V D K S R W Q Q
hIgG3          T T P P M L D S -- -- -- -- G S F F L Y S K L T V D K S R W Q Q
hIgG4        → T T P P V L D S -- -- -- -- G S F F L Y S R L T V D K S R W Q E mIgG1          N T Q P I M D T -- -- -- -- G S Y F V Y S K L N V Q K S N W E A
mIgE           N T A T V L D S -- -- -- -- G S Y F M Y S K L R V R K S T W E R
mIgG2A         B T A P V L D S -- -- -- -- G S Y F I Y S K L N M K T S K W E K
mIgG2B         N T P P I L D S -- -- -- -- G T Y F L Y S K L T V D T D S W L Q
mIgG3
             ************************************************************
                                                              480
             451                        470
hIgG1        G N V F S C S V M H E A L H N H Y T Q K S L S L S P G K
hIgE         K D E F I C R A V H E A A S P S Q T V Q R A V S V N P G K
hIgG2        G N V F S C S V M H E A L H N H Y T Q K S L S L S P G K
hIgG3        G N I F S C S V M H E A L H N R F T Q K S L S L S P G K
hIgG4        G N V F S C S V M H E A L H N H Y T Q K S L S L S L G K mIgG1        G N T F T C S V L H E G L H N H H T E K S L S H S P G K
mIgG2A       G S L F A C C N V V H E G L H N H H T T K T F S R S L G K
mIgG2B       T D S F S C N V R H E G L K N Y Y L K K T T I S R S P G K
mIgG3        G E I F T C S V V H E A L H N H H T Q K N L S R S P G K
             ************************************************************
```

T366Y:F405A/
T394W:Y407T ns a carcino-
KNOBS AND HOLES HETEROMERIC POLYPEPTIDES

RELATED APPLICATIONS

This application is a continuation of application Ser. No. 10/010,245 filed Dec. 7, 2001, which is a continuation of application Ser. No. 08/974,183 filed Nov. 19, 1997, now abandoned, which is a continuation of application Ser. No. 08/399,106 filed Mar. 1, 1995 (now U.S. Pat. No. 5,731,168 issued Mar. 24, 1998), all of which are incorporated herein by reference and to which priority is claimed under 35 USC §120.

INCORPORATION OF SEQUENCE LISTING

This application includes a Sequence Listing submitted via EFS-Web as a computer-readable form 15 kilobyte file entitled "GNE0321C.txt" created on Jul. 10, 2009, which is hereby incorporated herein by reference in its entirety.

BACKGROUND OF THE INVENTION

1. Field of the Invention

This invention relates to a method for making heteromultimeric polypeptides such as multispecific antibodies (e.g. bispecific antibodies), multispecific immunoadhesins (e.g. bispecific immunoadhesins) as well as antibody-immunoadhesin chimeras and the heteromultimeric polypeptides made using the method.

2. Description of Related Art

Bispecific Antibodies

Bispecific antibodies (BsAbs) which have binding specificities for at least two different antigens have significant potential in a wide range of clinical applications as targeting agents for in vitro and in vivo immunodiagnosis and therapy, and for diagnostic immunoassays.

In the diagnostic areas, bispecific antibodies have been very useful in probing the functional properties of cell surface molecules and in defining the ability of the different Fc receptors to mediate cytotoxicity (Fanger et al., *Crit. Rev. Immunol.* 12:101-124 [1992]). Nolan et al., *Biochem. Biophys. Acta.* 1040:1-11 (1990) describe other diagnostic applications for BsAbs. In particular, BsAbs can be constructed to immobilize enzymes for use in enzyme immunoassays. To achieve this, one arm of the BsAb can be designed to bind to a specific epitope on the enzyme so that binding does not cause enzyme inhibition, the other arm of the BsAb binds to the immobilizing matrix ensuring a high enzyme density at the desired site. Examples of such diagnostic BsAbs include the rabbit anti-IgG/anti-ferritin BsAb described by Hammerling et al., *J. Exp. Med.* 128:1461-1473 (1968) which was used to locate surface antigens. BsAbs having binding specificities for horse radish peroxidase (HRP) as well as a hormone have also been developed. Another potential immunochemical application for BsAbs involves their use in two-site immunoassays. For example, two BsAbs are produced binding to two separate epitopes on the analyte protein—one BsAb binds the complex to an insoluble matrix, the other binds an indicator enzyme (see Nolan et al., supra).

Bispecific antibodies can also be used for in vitro or in vivo immunodiagnosis of various diseases such as cancer (Songsivilai et al., *Clin. Exp. Immunol.* 79:315 [1990]). To facilitate this diagnostic use of the BsAb, one arm of the BsAb can bind a tumor associated antigen and the other arm can bind a detectable marker such as a chelator which tightly binds a radionuclide. Using this approach, Le Doussal et al. made a BsAb useful for radioimmunodetection of colorectal and thyroid carcinomas which had one arm which bound a carcinoembryonic antigen (CEA) and another arm which bound diethylenetriaminepentacetic acid (DPTA). See Le Doussal et al., *Int. J. Cancer Suppl.* 7:58-62 (1992) and Le Doussal et al., *J. Nucl. Med.* 34:1662-1671 (1993). Stickney et al. similarly describe a strategy for detecting colorectal cancers expressing CEA using radioimmunodetection. These investigators describe a BsAb which binds CEA as well as hydroxyethylthiourea-benzyl-EDTA (EOTUBE). See Stickney et al., *Cancer Res.* 51:6650-6655 (1991).

Bispecific antibodies can also be used for human therapy in redirected cytotoxicity by providing one arm which binds a target (e.g. pathogen or tumor cell) and another arm which binds a cytotoxic trigger molecule, such as the T-cell receptor or the Fcγ receptor. Accordingly, bispecific antibodies can be used to direct a patient's cellular immune defense mechanisms specifically to the tumor cell or infectious agent. Using this strategy, it has been demonstrated that bispecific antibodies which bind to the FcγRIII (i.e. CD16) can mediate tumor cell killing by natural killer (NK) cell/large granular lymphocyte (LGL) cells in vitro and are effective in preventing tumor growth in vivo. Segal et al., *Chem. Immunol.* 47:179 (1989) and Segal et al., *Biologic Therapy of Cancer* 2(4) DeVita et al. eds. J. B. Lippincott, Philadelphia (1992) p. 1. Similarly, a bispecific antibody having one arm which binds FcγRIII and another which binds to the HER2 receptor has been developed for therapy of ovarian and breast tumors that overexpress the HER2 antigen. (Hseih-Ma et al. *Cancer Research* 52:6832-6839 [1992] and Weiner et al. *Cancer Research* 53:94-100 [1993]). Bispecific antibodies can also mediate killing by T cells. Normally, the bispecific antibodies link the CD3 complex on T cells to a tumor-associated antigen. A fully humanized F(ab')$_2$ BsAb consisting of anti-CD3 linked to anti-p185$^{HER2}$ has been used to target T cells to kill tumor cells overexpressing the HER2 receptor. Shalaby et al., *J. Exp. Med.* 175(1):217 (1992). Bispecific antibodies have been tested in several early phase clinical trials with encouraging results. In one trial, 12 patients with lung, ovarian or breast cancer were treated with infusions of activated T-lymphocytes targeted with an anti-CD3/anti-tumor (MOC31) bispecific antibody. deLeij et al. *Bispecific Antibodies and Targeted Cellular Cytotoxicity*, Romet-Lemonne, Fanger and Segal Eds., Lienhart (1991) p. 249. The targeted cells induced considerable local lysis of tumor cells, a mild inflammatory reaction, but no toxic side effects or anti-mouse antibody responses. In a very preliminary trial of an anti-CD3/anti-CD19 bispecific antibody in a patient with B-cell malignancy, significant reduction in peripheral tumor cell counts was also achieved. Clark et al. *Bispecific Antibodies and Targeted Cellular Cytotoxicity*, Romet-Lemonne, Fanger and Segal Eds., Lienhart (1991) p. 243. See also Kroesen et al., *Cancer Immunol. Immunother.* 37:400-407 (1993), Kroesen et al., *Br. J. Cancer* 70:652-661 (1994) and Weiner et al., *J. Immunol.* 152:2385 (1994) concerning therapeutic applications for BsAbs.

Bispecific antibodies may also be used as fibrinolytic agents or vaccine adjuvants. Furthermore, these antibodies may be used in the treatment of infectious diseases (e.g. for targeting of effector cells to virally infected cells such as HIV or influenza virus or protozoa such as *Toxoplasma gondii*), used to deliver immunotoxins to tumor cells, or target immune complexes to cell surface receptors (see Fanger et al., supra).

Use of BsAbs has been effectively stymied by the difficulty of obtaining BsAbs in sufficient quantity and purity. Traditionally, bispecific antibodies were made using hybrid-hybridoma technology (Millstein and Cuello, *Nature* 305:537-539 [1983]). Because of the random assortment of immunoglobulin heavy and light chains, these hybridomas (quadromas) produce a potential mixture of 10 different antibody molecules, of which only one has the correct bispecific structure (see FIG. 1 herein). The purification of the correct molecule, which is usually done by affinity chromatography steps, is rather cumbersome, and the product yields are low. Accordingly, techniques for the production of greater yields of BsAb have been developed. These are depicted in FIGS. 2A-2E herein. As shown in FIG. 2A, bispecific antibodies can be prepared using chemical linkage. To achieve chemical coupling of antibody fragments, Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*. which can be chemically coupled to form bispecific antibodies (see FIG. 2B). Shalaby et al., *J. Exp. Med.* 175:217-225 (1992) describe the production of a fully humanized BsAb F(ab')$_2$ molecule having one arm which binds p185$^{HER2}$ and another arm which binds CD3. Each Fab' fragment was separately secreted from *E. coli*. and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J. Cancers* (Suppl.) 7:45-50 (1992).

Various techniques for making and isolating BsAb fragments directly from recombinant cell cultures have also been described. For example, bispecific F(ab')$_2$ heterodimers have been produced using leucine zippers (see FIG. 2C). Kostelny et al., *J. Immunol.* 148(5):1547-1553 (1992). The leucine zipper peptides from the Fos and Jun proteins were linked to the Fab' portions of anti-CD3 and anti-interleukin-2 receptor (IL-2R) antibodies by gene fusion. The antibody homodimers were reduced at the hinge region to form monomers and then reoxidized to form the antibody heterodimers. The BsAbs were found to be highly effective in recruiting cytotoxic T cells to lyse HuT-102 cells in vitro. The advent of the "diabody" technology described by Hollinger et al., *PNAS (USA)* 90:6444-6448 (1993) has provided an alternative mechanism for making BsAb fragments. The fragments comprise a heavy chain variable domain ($V_H$) connected to a light chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites (see FIG. 2D herein). Another strategy for making BsAb fragments by the use of single chain Fv (sFv) dimers has also been reported. See Gruber et al. *J. Immunol.* 152: 5368 (1994). These researchers designed an antibody which comprised the $V_H$ and $V_L$ domains of an antibody directed against the T cell receptor joined by a 25 amino acid residue linker to the $V_H$ and $V_L$ domains of an anti-fluorescein antibody. The refolded molecule (see FIG. 2E herein) bound to fluorescein and the T cell receptor and redirected the lysis of human tumor cells that had fluorescein covalently linked to their surface.

It is apparent that several techniques for making bispecific antibody fragments which can be recovered directly from recombinant cell culture have been reported. However, full length BsAbs may be preferable to BsAb fragments for many clinical applications because of their likely longer serum half-life and possible effector functions.

Immunoadhesins

Immunoadhesins (Ia's) are antibody-like molecules which combine the binding domain of a protein such as a cell-surface receptor or a ligand (an "adhesin") with the effector functions of an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Immunoadhesins reported in the literature include fusions of the T cell receptor (Gascoigne et al., *Proc. Natl. Acad. Sci. USA* 84:2936-2940 [1987]); CD4 (Capon et al., *Nature* 337: 525-531 [1989]; Traunecker et al., *Nature* 339:68-70 [1989]; Zettmeissl et al., *DNA Cell Biol. USA* 9:347-353 [1990]; and Byrn et al., *Nature* 344:667-670 [1990]); L-selectin or homing receptor (Watson et al., *J. Cell. Biol.* 110:2221-2229 [1990]; and Watson et al., *Nature* 349:164-167 [1991]); CD44 (Aruffo et al., *Cell* 61:1303-1313 [1990]); CD28 and B7 (Linsley et al., *J. Exp. Med.* 173:721-730 [1991]); CTLA-4 (Lisley et al., *J. Exp. Med.* 174:561-569 [1991]); CD22 (Stamenkovic et al., *Cell* 66:1133-1144 [1991]); TNF receptor (Ashkenazi et al., *Proc. Natl. Acad. Sci. USA* 88:10535-10539 [1991]; Lesslauer et al., *Eur. J. Immunol.* 27:2883-2886 [1991]; and Peppel et al., *J. Exp. Med.* 174:1483-1489 [1991]); NP receptors (Bennett et al., *J. Biol. Chem.* 266: 23060-23067 [1991]); inteferon γ receptor (Kurschner et al., *J. Biol. Chem.* 267:9354-9360 [1992]); 4-1BB (Chalupny et al., *PNAS [USA]* 89:10360-10364 [1992]) and IgE receptor a (Ridgway and Gorman, *J. Cell. Biol. Vol.* 115, Abstract No. 1448 [1991]).

Examples of immunoadhesins which have been described for therapeutic use include the CD4-IgG immunoadhesin for blocking the binding of HIV to cell-surface CD4. Data obtained from Phase I clinical trials in which CD4-IgG was administered to pregnant women just before delivery suggests that this immunoadhesin may be useful in the prevention of maternal-fetal transfer of HIV. Ashkenazi et al., *Intern. Rev. Immunol.* 10:219-227 (1993). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi et al., supra). Immunoadhesins also have non-therapeutic uses. For example, the L-selectin receptor immunoadhesin was used as an reagent for histochemical staining of peripheral lymph node high endothelial venules (HEV). This reagent was also used to isolate and characterize the L-selectin ligand (Ashkenazi et al., supra).

If the two arms of the immunoadhesin structure have different specificities, the immunoadhesin is called a "bispecific immunoadhesin" by analogy to bispecific antibodies. Dietsch et al., *J. Immunol. Methods* 162:123 (1993) describe such a bispecific immunoadhesin combining the extracellular domains of the adhesion molecules, E-selectin and P-selectin. Binding studies indicated that the bispecific immunoglobulin fusion protein so formed had an enhanced ability to bind to a myeloid cell line compared to the monospecific immunoadhesins from which it was derived.

Antibody-Immunoadhesin Chimeras

Antibody-immunoadhesin (Ab/Ia) chimeras have also been described in the literature. These molecules combine the binding region of an immunoadhesin with the binding domain of an antibody.

Berg et al., *PNAS (USA)* 88:4723-4727 (1991) made a bispecific antibody-immunoadhesin chimera which was derived from murine CD4-IgG. These workers constructed a tetrameric molecule having two arms. One arm was composed of CD4 fused with an antibody heavy-chain constant domain along with a CD4 fusion with an antibody light-chain constant domain. The other arm was composed of a complete heavy-chain of an anti-CD3 antibody along with a complete light-chain of the same antibody. By virtue of the CD4-IgG arm, this bispecific molecule binds to CD3 on the surface of cytotoxic T cells. The juxtaposition of the cytotoxic cells and HIV-infected cells results in specific killing of the latter cells.

While Berg et al. describe a bispecific molecule that was tetrameric in structure, it is possible to produce a trimeric hybrid molecule that contains only one CD4-IgG fusion. See Chamow et al., *J. Immunol.* 153:4268 (1994). The first arm of this construct is formed by a humanized anti-CD3 κ light chain and a humanized anti-CD3 γ heavy chain. The second arm is a CD4-IgG immunoadhesin which combines part of the extracellular domain of CD4 responsible for gp120 binding with the Fc domain of IgG. The resultant Ab/Ia chimera mediated killing of HIV-infected cells using either pure cytotoxic T cell preparations or whole peripheral blood lymphocyte (PBL) fractions that additionally included Fc receptor-bearing large granular lymphocyte effector cells.

In the manufacture of the above-mentioned heteromultimers, it is desirable to increase the yields of the desired heteromultimer over the homomultimer(s). The invention described herein provides a means for achieving this.

SUMMARY OF THE INVENTION

This application describes a "protuberance-into-cavity" strategy which serves to engineer an interface between a first and second polypeptide for hetero-oligomerization. See FIG. 4 for a schematic illustration of the strategy employed. The preferred interface comprises at least a part of the $C_H3$ domain of an antibody constant domain. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface.

Accordingly, the invention can be said to relate to a method of preparing a heteromultimer comprising a first polypeptide and a second polypeptide which meet at an interface, wherein the first polypeptide has a protuberance at the interface thereof which is positionable in a cavity at the interface of the second polypeptide. In one aspect, the method involves: (a) culturing a host cell comprising nucleic acid encoding the first polypeptide and second polypeptide, wherein the nucleic acid encoding the first polypeptide has been altered from the original nucleic acid to encode the protuberance or the nucleic acid encoding the second polypeptide has been altered from the original nucleic acid to encode the cavity, or both, such that the nucleic acid is expressed; and (b) recovering the heteromultimer from the host cell culture.

Normally, the nucleic acid encoding both the first polypeptide and the second polypeptide are altered to encode the protuberance and cavity, respectively. Preferably the first and second polypeptides each comprise an antibody constant domain such as the $C_H3$ domain of a human $IgG_1$.

The invention also provides a heteromultimer (such as a bispecific antibody, bispecific immunoadhesin or antibody/immunoadhesin chimera) comprising a first polypeptide and a second polypeptide which meet at an interface. The interface of the first polypeptide comprises a protuberance which is positionable in a cavity in the interface of the second polypeptide, and the protuberance or cavity, or both, have been introduced into the interface of the first and second polypeptides respectively. The heteromultimer may be provided in the form of a composition further comprising a pharmaceutically acceptable carrier.

The invention also relates to a host cell comprising nucleic acid encoding the heteromultimer of the preceding paragraph wherein the nucleic acid encoding the first polypeptide and second polypeptide is present in a single vector or in separate vectors. The host cell can be used in a method of making a heteromultimer which involves culturing the host cell so that the nucleic acid is expressed and recovering the heteromultimer from the cell culture.

In yet a further aspect, the invention provides a method of preparing a heteromultimer comprising:

(a) altering a first nucleic acid encoding a first polypeptide so that an amino acid residue in the interface of the first polypeptide is replaced with an amino acid residue having a larger side chain volume, thereby generating a protuberance on the first polypeptide;

(b) altering a second nucleic acid encoding a second polypeptide so that an amino acid residue in the interface of the second polypeptide is replaced with an amino acid residue having a smaller side chain volume, thereby generating a cavity in the second polypeptide, wherein the protuberance is positionable in the cavity;

(c) introducing into a host cell the first and second nucleic acids and culturing the host cell so that expression of the first and second nucleic acid occurs; and (d) recovering the heteromultimer formed from the cell culture.

The invention provides a mechanism for increasing the yields of the heteromultimer over other unwanted end-products such as homomultimers. Preferably, the yields of the heteromultimer recovered from recombinant cell culture are at least greater than 80% and preferably greater than 90% compared to the by-product homomultimer(s).

BRIEF DESCRIPTION OF THE DRAWINGS

FIG. 1 depicts the various antibody molecules which may be generated when the traditional hybrid-hybridoma technique of Millstein and Cuello, supra, is used for making full length BsAbs.

FIG. 5 shows the interface residues of the C$_H$3 domain of the immunoglobulins IgG (SEQ ID NO: 2), IgA (SEQ ID NO: 3), IgD (SEQ ID NO: 4), IgE (SEQ ID NO: 5) and IgM (SEQ ID NO: 6). The C$_H$3 domain of each of these immunoglobulins is made up of a "β-sandwich", which is comprised of two separate and parallel "β-sheets". One of the β-sheets provides the interface residues, the other is the "exterior β-sheet". The β-sheet forming the interface is formed from four "β-strands". The residues of each of the seven β-strands of the C$_H$3 domain of the various immunoglobulins are identified by dashed overlining. The residues in the middle and edge β-strands of the interface are identified, as are those of the exterior β-sheet. Residue numbering is according to Fc crystal structure (Deisenhofer, Biochem. 20:2361 [1981]). The residues buried in the interior of the C$_H$3 domain are identified with a 'B', those which are partially buried in the interior of the C$_H$3 domain are identified with a "b", those "contact" residues which are partially buried at the interface (i.e. 26%-10% exposed) are identified with an "i" and those which are buried at the interface (i.e. <6% exposed) are identified with an "I". The bold residues are optimal candidate original residues for replacement with import residues.

FIG. 6 identifies the interface residues of human (h) ('hI2G1', 'hI2G2', 'hI2G3', 'hI2G4' and 'hI2E' disclosed as SEQ ID NOS: 7-10 and 15, respectively, in order of appearance) or murine (m) ('mI2G1', 'mI2G2A', 'mI2G2B' and 'mI2G3' disclosed as SEQ ID NOS: 11-14, respectively, in order of appearance) IgG subtypes (B=ASX and Z=GLX). The residues in β-strands at the edge and middle of the interface are bracketed and "contact" residues are indicated with arrows. Sequences obtained from Miller et al., *J. Mol. Biol.* 216:965 (1990) and Kabat et al., *Sequences of Proteins of Immunological Interest*, National Institutes of Health, Bethesda, Md., ed. 5, (1991). It is apparent that the contact residues are highly conserved.

FIG. 10A shows wild-type; FIG. 10B shows mutant Ab Y407T, Ia T366Y; FIG. 10C shows mutant Ab T366Y, Ia Y407T; FIG. 10D shows mutant Ab F405A, Ia T394W; and FIG. 10E shows mutant Ab T366Y:F405A, Ia T394W: Y407T. Data presented are the mean from at least 2 independent experiments. The densitometric signal response was found to be linear (R=0.9993) over the experimental range used (0.02-10 μg) as judged by control experiment using a closely related humanized antibody, huMAb4D5-8 (Carter et al., *Proc. Natl. Acad. Sci. USA* 89:4285 [1992]).

I. Definitions

Figure 2A:
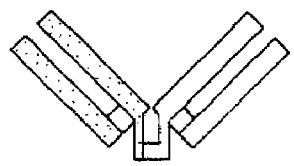
FIGS. 2A-2E illustrate the various techniques of the background art for manufacturing BsAb fragments, reviewed in the background section above.
Figure 2B:
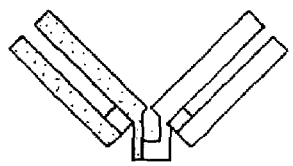
Figure 2C:
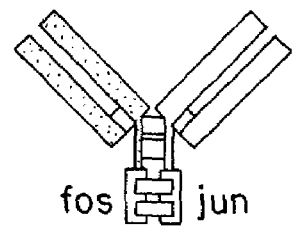
Figure 2E:
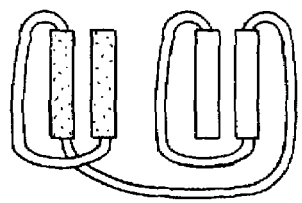
Figure 2D:
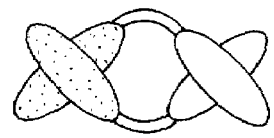

In general, the following words or phrases have the indicated definitions when used in the description, examples, and claims:

A "heteromultimer" or "heteromultimeric polypeptide" is a molecule comprising at least a first polypeptide and a second polypeptide, wherein the second polypeptide differs in amino acid sequence from the first polypeptide by at least one amino acid residue. Preferably, the heteromultimer has binding specificity for at least two different ligands or binding sites. The heteromultimer can comprise a "heterodimer" formed by the first and second polypeptide or can form higher order tertiary structures where polypeptides in addition to the first and second polypeptide are present. Exemplary structures for the heteromultimer include heterodimers (e.g. the bispecific immunoadhesin described by Dietsch et al., supra), heterotrimers (e.g. the Ab/Ia chimera described by Chamow et al., supra), heterotetramers (e.g. a bispecific antibody) and further oligomeric structures.

As used herein, "polypeptide" refers generally to peptides and proteins having more than about ten amino acids. Preferably, mammalian polypeptides (polypeptides that were originally derived from a mammalian organism) are used, more preferably those which are directly secreted into the medium. Examples of bacterial polypeptides include, e.g., alkaline phosphatase and β-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The "first polypeptide" is any polypeptide which is to be associated with a second polypeptide. The first and second polypeptide meet at an "interface" (defined below). In addition to the interface, the first polypeptide may comprise one or more additional domains, such as "binding domains" (e.g. an antibody variable domain, receptor binding domain, ligand binding domain or enzymatic domain) or antibody constant domains (or parts thereof) including $C_H2$, $C_H1$ and $C_L$ domains. Normally, the first polypeptide will comprise at least one domain which is derived from an antibody. This domain conveniently is a constant domain, such as the $C_H3$ domain of an antibody and can form the interface of the first polypeptide. Exemplary first polypeptides include antibody heavy chain polypeptides, chimeras combining an antibody constant domain with a binding domain of a heterologous polypeptide (i.e. an immunoadhesin, see definition below), receptor polypeptides (especially those which form dimers with another receptor polypeptide, e.g., interleukin-8 receptor [IL-8R] and integrin heterodimers [e.g. LFA-1 or GPIIIb/IIIa]), ligand polypeptides (e.g. nerve growth factor [NGF], neurotrophin-3 [NT-3], and brain-derived neurotrophic factor [BDNF]—see Arakawa et al. *J. Biol. Chem.* 269(45): 27833-27839 [1994] and Radziejewski et al. *Biochem.* 32(48): 1350 [1993]) and antibody variable domain polypeptides (e.g. diabodies). The preferred first polypeptide is selected from an antibody heavy chain and an immunoadhesin.

The "second polypeptide" is any polypeptide which is to be associated with the first polypeptide via an "interface". In addition to the interface, the second polypeptide may comprise additional domains such as a "binding domain" (e.g. an antibody variable domain, receptor binding domain, ligand binding domain or enzymatic domain), or antibody constant domains (or parts thereof) including $C_H2$, $C_H1$ and $C_L$ domains. Normally, the second polypeptide will comprise at least one domain which is derived from an antibody. This domain conveniently is a constant region, such as the $C_H3$ domain of an antibody and can form the interface of the second polypeptide. Exemplary second polypeptides include antibody heavy chain polypeptides, chimeras combining an antibody constant domain with a binding domain of a heterologous polypeptide (i.e. an immunoadhesin, see definition below), receptor polypeptides (especially those which form dimers with another receptor polypeptide, e.g., interleukin-8 receptor [IL-8R] and integrin heterodimers e[g. LFA-1 or GPIIIb/IIIa]), ligand polypeptides (e.g. nerve growth factor [NGF], neurotrophin-3 [NT-3], and brain-derived neurotrophic factor [BDNF]—see Arakawa et al. *J. Biol. Chem.* 269(45): 27833-27839 [1994] and Radziejewski et al. *Biochem.* 32(48): 1350 [1993]) and antibody variable domain polypeptides (e.g. diabodies). The preferred second polypeptide is selected from an antibody heavy chain and an immunoadhesin.

A "binding domain" comprises any region of a polypeptide which is responsible for selectively binding to a molecule of interest (e.g. an antigen, ligand, receptor, substrate or inhibitor). Exemplary binding domains include an antibody variable domain, receptor binding domain, ligand binding domain and an enzymatic domain.

The term "antibody" shall mean a polypeptide containing one or more domains capable of binding an epitope on an antigen of interest, where such domain(s) are derived from or homologous with the variable region of an antibody. Examples of antibodies include full length antibodies, antibody fragments, single chain molecules, bispecific or bifunctional molecules, diabodies, and chimeric antibodies (e.g. humanized and Primatized™ antibodies). "Antibody fragments" include Fv, Fv', Fab, Fab', and F(ab')$_2$ fragments.

"Humanized" forms of non-human (e.g. rodent or primate) antibodies are specific chimeric immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. The humanized antibody includes a Primatized™ antibody wherein the antigen-binding region of the antibody is derived from an antibody produced by immunizing macaque monkeys with the antigen of interest.

A "multispecific antibody" is a molecule having binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/ anti-DPTA, anti-p185$^{HER2}$/anti-hapten; BsAbs as vaccine adjuvants (see Fanger et al., supra); and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan et al., supra). Examples of trispecific antibodies include anti-CD3/anti-CD4/anti-CD37, anti-CD3/anti-CD5/anti-CD37 and anti-CD3/anti-CD8/anti-CD37.

As used herein, the term "immunoadhesin" designates antibody-like molecules which combine the "binding domain" of a heterologous protein (an "adhesin", e.g. a receptor, ligand or enzyme) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG$_1$, IgG$_2$, IgG$_3$, or IgG$_4$ subtypes, IgA, IgE, IgD or IgM.

The term "ligand binding domain" as used herein refers to any native cell-surface receptor or any region or derivative thereof retaining at least a qualitative ligand binding ability, and preferably the biological activity of a corresponding native receptor. In a specific embodiment, the receptor is from a cell-surface polypeptide having an extracellular domain which is homologous to a member of the immunoglobulin supergenefamily. Other typical receptors, are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability, and preferably the biological activity of a corresponding native ligand. This definition, among others, specifically includes binding sequences from ligands for the above-mentioned receptors.

As used herein the phrase "multispecific immunoadhesin" designates immunoadhesins (as hereinabove defined) having at least two binding specificities (i.e. combining two or more adhesin binding domains). Multispecific immunoadhesins can be assembled as heterodimers, heterotrimers or heterotetramers, essentially as disclosed in WO 89/02922 (published 6 Apr. 1989), in EP 314,317 (published 3 May 1989), and in U.S. Pat. No. 5,116,964 issued 2 May 1992. Preferred multispecific immunoadhesins are bispecific. Examples of bispecific immunoadhesins include CD4-IgG/TNFreceptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

An "antibody-immunoadhesin chimera (Ab/Ia chimera)" comprises a molecule which combines at least one binding domain of an antibody (as herein defined) with at least one immunoadhesin (as defined in this application). Exemplary Ab/Ia chimeras are the bispecific CD4-IgG chimeras described by Berg et al., supra and Chamow et al., supra.

The "interface" comprises those "contact" amino acid residues (or other non-amino acid groups such as carbohydrate groups, NADH, biotin, FAD or haem group) in the first polypeptide which interact with one or more "contact" amino acid residues (or other non-amino acid groups) in the interface of the second polypeptide. The preferred interface is a domain of an immunoglobulin such as a variable domain or constant domain (or regions thereof), however the interface between the polypeptides forming a heteromultimeric receptor or the interface between two or more ligands such as NGF, NT-3 and BDNF are included within the scope of this term. The preferred interface comprises the C$_H$3 domain of an immunoglobulin which preferably is derived from an IgG antibody and most preferably an human IgG$_1$ antibody.

A "protuberance" refers to at least one amino acid side chain which projects from the interface of the first polypeptide and is therefore positionable in a compensatory cavity in the adjacent interface (i.e. the interface of the second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE 1

Properties of Amino Acid Residues

| Amino Acid | One-Letter Abbreviation | MASS[a] (daltons) | VOLUME[b] (Å$^3$) | Accessible Surface Area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from Handbook of Chemistry and Physics, 43rd ed. Cleveland, Chemical Rubber Publishing Co., 1961.
[b]Values from A. A. Zamyatnin, Prog. Biophys. Mol. Biol. 24: 107–123, 1972.
[c]Values from C. Chothia, J. Mol. Biol. 105: 1–14, 1975. The accessible surface area is defined in FIGS. 6–20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In the preferred embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of the second polypeptide and therefore accommodates a corresponding protuberance on the adjacent interface of the first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 1 above. The preferred import residues for the formation of a cavity are usually naturally occurring amino acid residues and are preferably selected from alanine (A), serine (S), threonine (T) and valine (V). Most preferred are serine, alanine or threonine. In the preferred embodiment, the original residue for the formation of the protuberance has a large side chain volume, such as tyrosine, arginine, phenylalanine or tryptophan.

A "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 1 above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g. a humanized monoclonal antibody).

Preferably the import amino acid residue for forming the protuberance has a relatively small number of "rotamers" (e.g. about 3-6). A "rotomer" is an energetically favorable conformation of an amino acid side chain. The number of rotomers of the various amino acid residues are reviewed in Ponders and Richards, *J. Mol. Biol.* 193: 775-791 (1987).

"Isolated" heteromultimer means heteromultimer which has been identified and separated and/or recovered from a component of its natural cell culture environment. Contaminant components of its natural environment are materials which would interfere with diagnostic or therapeutic uses for the heteromultimer, and may include enzymes, hormones, and other proteinaceous or nonproteinaceous solutes. In preferred embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homomultimers). Expressed in terms of purity, substantial homogeneity means that the amount of by-products does not exceed 10%, and preferably is below 5%, more preferably below 1%, most preferably below 0.5%, wherein the percentages are by weight.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

II. Preparation of the Heteromultimer

1. Preparation of the Starting Materials

As a first step, the first and second polypeptide (and any additional polypeptides forming the heteromultimer) are selected. Normally, the nucleic acid encoding these polypeptides needs to be isolated so that it can be altered to encode the protuberance or cavity, or both, as herein defined. However, the mutations can be introduced using synthetic means, e.g. by using a peptide synthesizer. Also, in the case where the import residue is a non-naturally occurring residue, the method of Noren et al., supra is available for making polypeptides having such substitutions. Additionally, part of the heteromultimer is suitably made recombinantly in cell culture and other part(s) of the molecule are made by those techniques mentioned above.

Techniques for isolating antibodies and preparing immunoadhesins follow. However, it will be appreciated that the heteromultimer can be formed from, or incorporate, other polypeptides using techniques which are known in the art. For example, nucleic acid encoding a polypeptide of interest (e.g. a ligand, receptor or enzyme) can be isolated from a cDNA library prepared from tissue believed to possess the polypeptide mRNA and to express it at a detectable level. Libraries are screened with probes (such as antibodies or oligonucleotides of about 20-80 bases) designed to identify the gene of interest or the protein encoded by it. Screening the cDNA or genomic library with the selected probe may be conducted using standard procedures as described in chapters 10-12 of Sambrook et al., *Molecular Cloning: A Laboratory Manual* (New York: Cold Spring Harbor Laboratory Press, 1989).

(i) Antibody Preparation

Several techniques for the production of antibodies have been described which include the traditional hybridoma method for making monoclonal antibodies, recombinant techniques for making antibodies (including chimeric antibodies, e.g. humanized antibodies), antibody production in transgenic animals and the recently described phage display technology for preparing "fully human" antibodies. These techniques shall be described briefly below.

Polyclonal antibodies to the antigen of interest generally can be raised in animals by multiple subcutaneous (sc) or intraperitoneal (ip) injections of the antigen and an adjuvant. It may be useful to conjugate the antigen (or a fragment containing the target amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N\!=\!C\!=\!NR$, where R and $R^1$ are different alkyl groups. Animals are immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies using the hybridoma method first described by Kohler & Milstein, *Nature* 256:495 (1975) or may be made by recombinant DNA methods (Cabilly et al., U.S. Pat. No. 4,816,567). In the hybridoma method, a mouse or other appropriate host animal, such as hamster, is immunized as hereinabove described to elicit lymphocytes that produce, or are capable of producing, antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 [Academic Press, 1986]). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 [1984]; and Brodeur et al., *Monoclonal Antibody Production Techniques and Applications*, pp. 51-63, Marcel Dekker, Inc., New York, 1987). See, also, Boerner et al., *J. Immunol.*, 147(1):86-95 (1991) and WO 91/17769, published Nov. 28, 1991, for techniques for the production of human monoclonal antibodies. Culture medium in which hybridoma cells are growing is assayed for production of monoclonal antibodies directed against the antigen of interest. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson & Pollard, *Anal. Biochem.* 107:220 (1980). After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551-255 (1993) and Jakobovits et al., *Nature* 362:255-258 (1993).

In a further embodiment, antibodies or antibody fragments can be isolated from antibody phage libraries generated using the techniques described in McCafferty et al., *Nature*, 348: 552-554 (1990), using the antigen of interest to select for a suitable antibody or antibody fragment. Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Mark et al., *Bio/Technol.* 10:779-783 [1992]), as well as combinatorial infection and in vivo recombination as a strategy for constructing very large phage libraries (Waterhouse et al., *Nuc. Acids Res.*, 21:2265-2266 [1993]). Thus, these techniques are viable alternatives to traditional monoclonal antibody hybridoma techniques for isolation of "monoclonal" antibodies (especially human antibodies) which are encompassed by the present invention.

DNA encoding the antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81:6851 (1984). In that manner, "chimeric" antibodies are prepared that have the binding specificity of an anti-antigen monoclonal antibody herein.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522-525 [1986]; Riechmann et al., *Nature* 332:323-327 [1988]; Verhoeyen et al., *Science* 239:1534-1536 [1988]), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues, and possibly some FR residues, are substituted by residues from analogous sites in rodent antibodies. It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. For further details see WO 92/22653, published Dec. 23, 1992.

(ii) Immunoadhesin Preparation

Immunoglobulins (Ig) and certain variants thereof are known and many have been prepared in recombinant cell culture. For example, see U.S. Pat. No. 4,745,055; EP 256, 654; Faulkner et al., *Nature* 298:286 (1982); EP 120,694; EP 125,023; Morrison, *J. Immun.* 123:793 (1979); Köhler et al., *Proc. Natl. Acad. Sci. USA* 77:2197 (1980); Raso et al., *Cancer Res.* 41:2073 (1981); Morrison et al., *Ann. Rev. Immunol.* 2:239 (1984); Morrison, *Science* 229:1202 (1985); Morrison et al., *Proc. Natl. Acad. Sci. USA* 81:6851 (1984); EP 255, 694; EP 266,663; and WO 88/03559. Reassorted immunoglobulin chains also are known. See, for example, U.S. Pat. No. 4,444,878; WO 88/03565; and EP 68,763 and references cited therein.

Chimeras constructed from an adhesin binding domain sequence linked to an appropriate immunoglobulin constant domain sequence (immunoadhesins) are known in the art. Immunoadhesins reported in the literature include fusions of the T cell receptor (Gascoigne et al., *Proc. Natl. Acad. Sci. USA* 84:2936-2940 [1987]); CD4 (Capon et al., *Nature* 337: 525-531 [1989]; Traunecker et al., *Nature* 339:68-70 [1989];

Zettmeissl et al., *DNA Cell Biol. USA* 9:347-353 [1990]; and Byrn et al., *Nature* 344:667-670 [1990]); L-selectin (homing receptor) (Watson et al., *J. Cell. Biol.* 110:2221-2229 [1990]; and Watson et al., *Nature* 349:164-167 [1991]); CD44 (Aruffo et al., *Cell* 61:1303-1313 [1990]); CD28 and B7 (Linsley et al., *J. Exp. Med.* 173:721-730 [1991]); CTLA-4 (Lisley et al., *J. Exp. Med.* 174:561-569 [1991]); CD22 (Stamenkovic et al., *Cell* 66:1133-1144 [1991]); TNF receptor (Ashkenazi et al., *Proc. Natl. Acad. Sci. USA* 88:10535-10539 [1991]; Lesslauer et al., *Eur. J. Immunol.* 27:2883-2886 [1991]; and Peppel et al., *J. Exp. Med.* 174:1483-1489 [1991]); and IgE receptor α (Ridgway and Gorman, *J. Cell. Biol.* Vol. 115, Abstract No. 1448 [1991]).

Figure 3A:
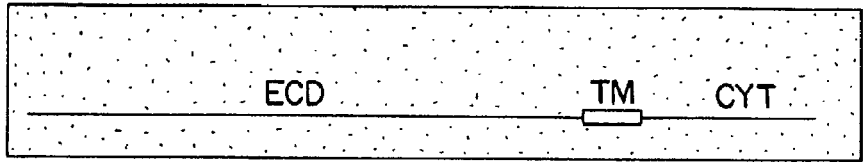
FIGS. 3A-3C depict an exemplary strategy for making an immunoadhesin dimer (SEQ ID NO: 1) (FIG. 3C) comprising the binding domain of a receptor (FIG. 3A) and the constant domain of an IgG$_1$ immunoglobulin (FIG. 3B).
Figure 3B:
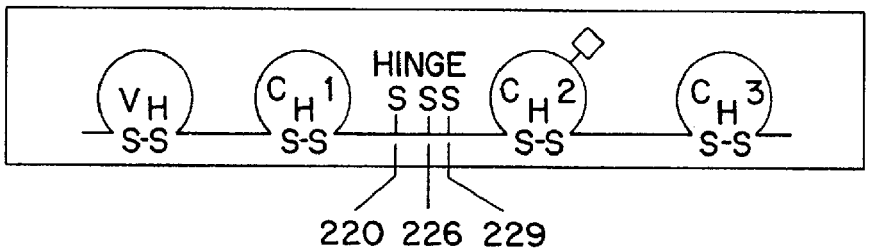
Figure 3C:
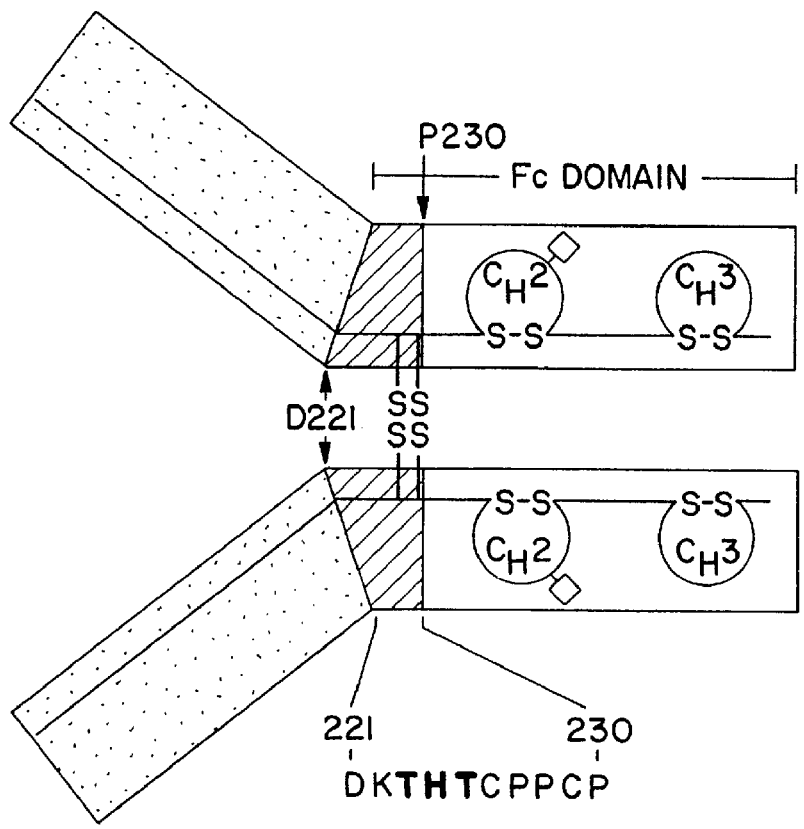
Figure 4:
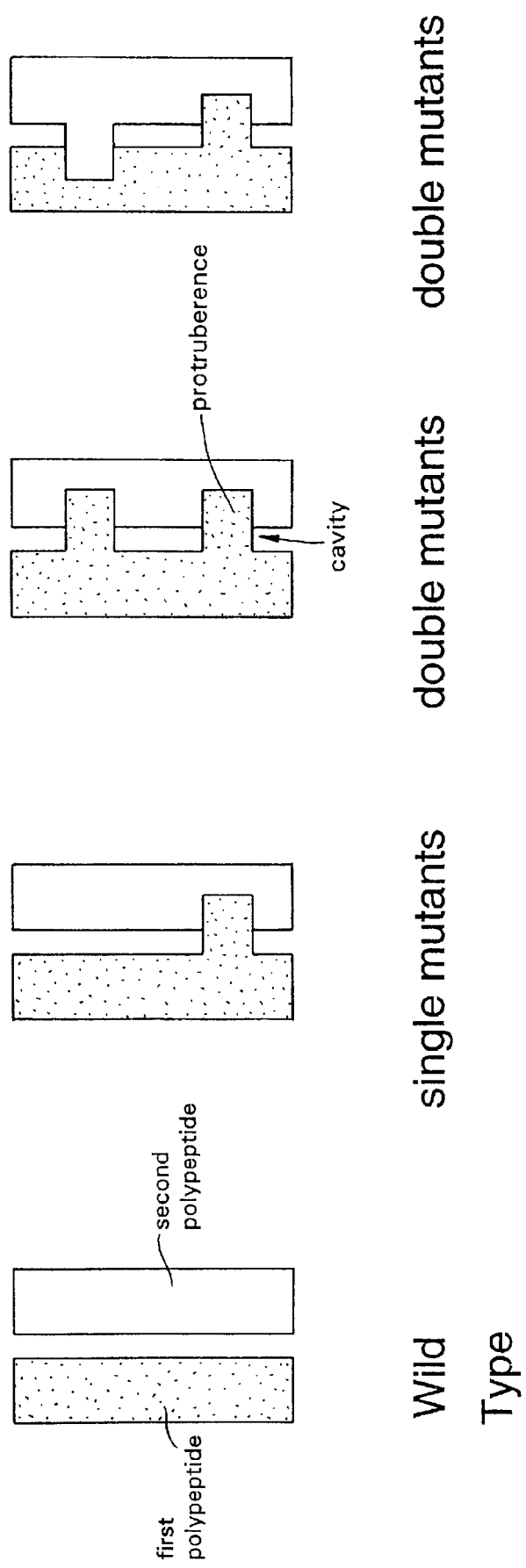
FIG. 4 illustrates schematically the protuberance-into-cavity strategy of the instant application for generating heteromultimers.

The simplest and most straightforward immunoadhesin design combines the binding domain(s) of the adhesin (e.g. the extracellular domain [ECD] of a receptor) with the hinge and Fc regions of an immunoglobulin heavy chain (see FIG. 3). Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the Ia.

In a preferred embodiment, the adhesin sequence is fused to the N-terminus of the Fc domain of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an $IgG_1$, $IgG_2$, or $IgG_3$ heavy chain. The precise site at which the fusion is made is not critical, and the optimal site can be determined by routine experimentation.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-[$AC_H$, $AC_L$-$AC_H$, $AC_L$-$V_HC_H$, or $V_LC_L$-$AC_H$];
(c) $AC_L$-$AC_H$-[$AC_L$-$AC_H$, $AC_L$-$V_HC_H$, $V_LC_L$-$AC_H$, or $V_LC_L$-$V_HC_H$];
(d) $AC_L$-$V_HC_H$-[$AC_H$, or $AC_L$-$V_HC_H$, or $V_LC_L$-$AC_H$];
(e) $V_LC_L$-$AC_H$-[$AC_LV_HC_H$, or $V_LC_L$-$AC_H$]; and
(f) $[A-Y]_n$-$[V_LC_L$-$V_HC_H]_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human $IgG_1$ and $IgG_3$ immunoglobulin sequences is preferred. A major advantage of using $IgG_1$ is that $IgG_1$ immunoadhesins can be purified efficiently on immobilized protein A. In contrast, purification of $IgG_3$ requires protein G, a significantly less versatile medium. However, other structural and functional properties of immunoglobulins should be considered when choosing the Ig fusion partner for a particular immunoadhesin construction. For example, the $IgG_3$ hinge is longer and more flexible, so it can accommodate larger "adhesin" domains that may not fold or function properly when fused to $IgG_1$. Another consideration may be valency; IgG immunoadhesins are bivalent homodimers, whereas Ig subtypes like IgA and IgM may give rise to dimeric or pentameric structures, respectively, of the basic Ig homodimer unit. For immunoadhesins designed for in vivo application, the pharmacokinetic properties and the effector functions specified by the Fc region are important as well. Although $IgG_1$, $IgG_2$ and $IgG_4$ all have in vivo half-lives of 21 days, their relative potencies at activating the complement system are different. $IgG_4$ does not activate complement, and $IgG_2$ is significantly weaker at complement activation than $IgG_1$. Moreover, unlike $IgG_1$, $IgG_2$ does not bind to Fc receptors on mononuclear cells or neutrophils. While $IgG_3$ is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG$_1$ has only four serologically-defined allotypic sites, two of which (G1m and 2) are located in the Fc region; and one of these sites, G1m1, is non-immunogenic. In contrast, there are 12 serologically-defined allotypes in IgG3, all of which are in the Fc region; only three of these sites (G3 m5, 11 and 21) have one allotype which is nonimmunogenic. Thus, the potential immunogenicity of a γ3 immunoadhesin is greater than that of a γ1 immunoadhesin.

Immunoadhesins are most conveniently constructed by fusing the cDNA sequence encoding the adhesin portion in-frame to an Ig cDNA sequence. However, fusion to genomic Ig fragments can also be used (see, e.g. Gascoigne et al., supra; Aruffo et al., Cell 61:1303-1313 [1990]; and Stamenkovic et al., Cell 66:1133-1144 [1991]). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the Ig parts of the immunoadhesin are inserted in tandem into a plasmid vector that directs efficient expression in the chosen host cells.

2. Generating a Protuberance and/or Cavity

As a first step to selecting original residues for forming the protuberance and/or cavity, the three-dimensional structure of the heteromultimer is obtained using techniques which are well known in the art such as X-ray crystallography or NMR. Based on the three-dimensional structure, those skilled in the art will be able to identify the interface residues.

Figure 7:
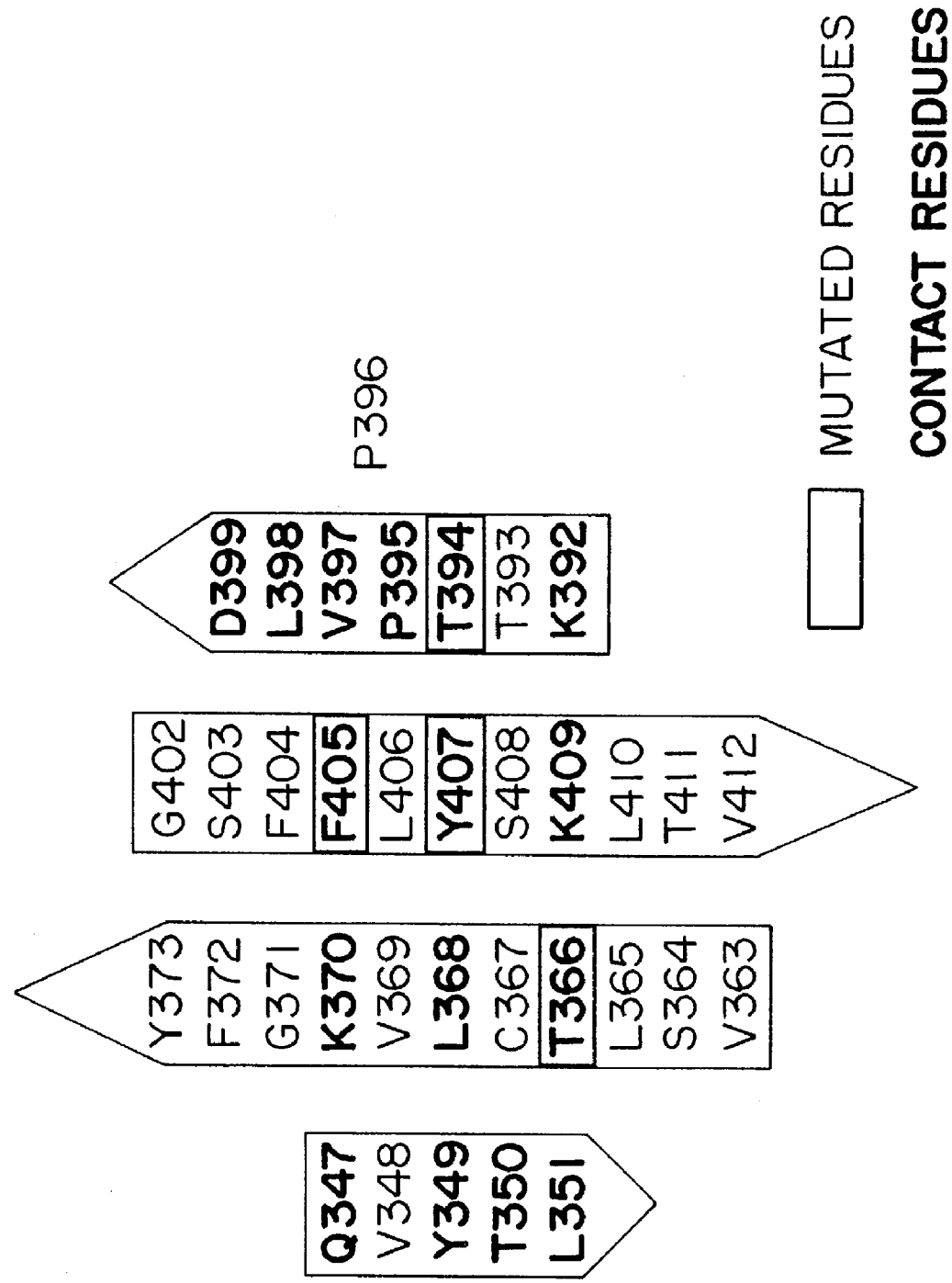
FIG. 7 shows the interface residues of the C$_H$3 domain of human IgG$_1$ (SEQ ID NOS 16-19, respectively, in order of appearance). Data derived from Miller et al., *J. Mol. Biol.* 216:965 (1990). "Contact" residues are shown and those residues mutated in the examples described herein are boxed.

The preferred interface is the $C_H3$ domain of an immunoglobulin constant domain. The interface residues of the $C_H3$ domains of IgG, IgA, IgD, IgE and IgM are identified in FIG. 5, including those which are optimal for replacing with import residues. The interface residues of various IgG subtypes are illustrated in FIG. 6. "Buried" residues are also identified. The basis for engineering the $C_H3$ interface is that X-ray crystallography has demonstrated that the intermolecular association between human IgG$_1$ heavy chains in the Fc region includes extensive protein/protein interaction between $C_H3$ domains whereas the glycosylated $C_H2$ domains interact via their carbohydrate (Deisenhofer, Biochem. 20:2361 [1981]). In addition there are two inter-heavy chain disulfide bonds which are efficiently formed during antibody expression in mammalian cells unless the heavy chain is truncated to remove $C_H2$ and $C_H3$ domains (King et al., Biochem. J. 281: 317 [1992]). Thus, heavy chain assembly appears to promote disulfide bond formation rather than vice versa. Taken together these structural and functional data led to the hypothesis that antibody heavy chain association is directed by the $C_H3$ domains. It was further speculated that the interface between $C_H3$ domains might be engineered to promote formation of heteromultimers of different heavy chains and hinder assembly of corresponding homomultimers. The experiments described herein demonstrated that it was possible to promote the formation of heteromultimers over homomultimers using this approach. Thus, it is possible to generate a polypeptide fusion comprising a polypeptide of interest and the $C_H3$ domain of an antibody to form a first or second polypeptide. The preferred $C_H3$ domain is derived from an IgG antibody, such as an human IgG$_1$. The interface residues of human IgG$_1$ are depicted in FIG. 7.

Those interface residues which can potentially constitute candidates for forming the protuberance or cavity are identified. It is preferable to select "buried" residues to be replaced. To determine whether a residue is buried, the surface accessibility program of Lee et al. J. Mol. Biol. 55: 379-400 (1971) can be used to calculate the solvent accessibility (SA) of residues in the interface. Then, the SA for the residues of each of the first and second polypeptide can be separately calculated after removal of the other polypeptide. The difference in SA of each residue between the monomer and dimer forms of the interface can then be calculated by: S A (dimer)-SA (monomer). This provides a list of residues which lose SA on formation of the dimer. The SA of each residue in the dimer is compared to the theoretical SA of the same amino acid in the tripeptide Gly-X-Gly, where X=the amino acid of interest (Rose et al. Science 229: 834-838 [1985]). Residues which (a) lost SA in the dimer compared to the monomer and (b) had an SA less than 26% of that in their corresponding tripeptide are considered as interface residues. Two categories may be delineated: those which have an SA<10% compared to their corresponding tripeptide (i.e. "buried") and those which have 25%>SA>10% compared to their corresponding tripeptide (i.e. "partially buried").

TABLE 2

| Residue No.† | SA Lost Monomer → Dimer | | % Tripeptide | |
|---|---|---|---|---|
| | Polypeptide A | Polypeptide B | Polypeptide A | Polypeptide B |
| Q347 | 22.1 | 31.0 | 25.0 | 26.5 |
| Y349 | 79.8 | 83.9 | 5.2 | 5.7 |
| L351 | 67.4 | 77.7 | 3.9 | 2.0 |
| S354 | 53.4 | 52.8 | 11.3 | 11.7 |
| E357 | 43.7 | 45.3 | 0.4 | 1.3 |
| S364 | 21.5 | 15.1 | 0.5 | 1.4 |
| T366 | 29.3 | 25.8 | 0.0 | 0.1 |
| L368 | 25.5 | 29.7 | 1.0 | 1.1 |
| K370 | 55.8 | 62.3 | 11.5 | 11.0 |
| T394 | 64.0 | 58.5 | 0.6 | 1.4 |
| V397 | 50.3 | 49.5 | 13.2 | 11.0 |
| D399 | 39.7 | 33.7 | 5.7 | 5.7 |
| F405 | 53.7 | 52.1 | 0.0 | 0.0 |
| Y407 | 89.1 | 90.3 | 0.0 | 0.0 |
| K409 | 86.8 | 92.3 | 0.7 | 0.6 |
| T411 | 4.3 | 7.5 | 12.7 | 9.8 |

†residue numbering as in IgG crystal structure (Deisenhofer, Biochemistry 20: 2361–2370 [1981]).

The effect of replacing residues on the polypeptide chain structure can be studied using a molecular graphics modeling program such as the Insight™ program (Biosym Technologies). Using the program, those buried residues in the interface of the first polypeptide which have a small side chain volume can be changed to residues having a larger side chain volume (i.e. a protuberance), for example. Then, the residues in the interface of the second polypeptide which are in proximity to the protuberance are examined to find a suitable residue for forming the cavity. Normally, this residue will have a large side chain volume and is replaced with a residue having a smaller side chain volume. In certain embodiments, examination of the three-dimensional structure of the interface will reveal a suitably positioned and dimensioned protuberance on the interface of the first polypeptide or a cavity on the interface of the second polypeptide. In these instances, it is only necessary to model a single mutant, i.e., with a synthetically introduced protuberance or cavity.

With respect to selecting potential original residues for replacement where the first and second polypeptide each comprise a $C_H3$ domain, the $C_H3/C_H3$ interface of human IgG$_1$ involves sixteen residues on each domain located on four anti-parallel β-strands which buries 1090 Å$^2$ from each surface (Deisenhofer, supra) and Miller, *J. Mol. Biol.* 216:965 [1990]). See FIG. 7 herein. Mutations are preferably targeted to residues located on the two central anti-parallel β-strands. The aim is to minimize the risk that the protuberances which are created can be accommodated by protruding into surrounding solvent rather than by compensatory cavities in the partner $C_H3$ domain.

Once the preferred original/import residues are identified by molecular modeling, the amino acid replacements are introduced into the polypeptide using techniques which are well known in the art. Normally the DNA encoding the polypeptide is genetically engineered using the techniques described in *Mutagenesis: a Practical Approach*, supra.

Oligonucleotide-mediated mutagenesis is a preferred method for preparing substitution variants of the DNA encoding the first or second polypeptide. This technique is well known in the art as described by Adelman et al., *DNA*, 2:183 (1983). Briefly, first or second polypeptide DNA is altered by hybridizing an oligonucleotide encoding the desired mutation to a DNA template, where the template is the single-stranded form of a plasmid or bacteriophage containing the unaltered or native DNA sequence of heteromultimer. After hybridization, a DNA polymerase is used to synthesize an entire second complementary strand of the template that will thus incorporate the oligonucleotide primer, and will code for the selected alteration in the heteromultimer DNA.

Cassette mutagenesis can be performed as described Wells et al. *Gene* 34:315 (1985) by replacing a region of the DNA of interest with a synthetic mutant fragment generated by annealing complimentary oligonucleotides. PCR mutagenesis is also suitable for making variants of the first or second polypeptide DNA. While the following discussion refers to DNA, it is understood that the technique also finds application with RNA. The PCR technique generally refers to the following procedure (see Erlich, *Science*, 252:1643-1650 [1991], the chapter by R. Higuchi, p. 61-70).

This invention also encompasses, in addition to the protuberance or cavity mutations, amino acid sequence variants of the heteromultimer which can be prepared by introducing appropriate nucleotide changes into the heteromultimer DNA, or by synthesis of the desired heteromultimer polypeptide. Such variants include, for example, deletions from, or insertions or substitutions of, residues within the amino acid sequences of the first and second polypeptides forming the heteromultimer. Any combination of deletion, insertion, and substitution is made to arrive at the final construct, provided that the final construct possesses the desired antigen-binding characteristics. The amino acid changes also may alter post-translational processes of the heteromultimer, such as changing the number or position of glycosylation sites.

A useful method for identification of certain residues or regions of the heteromultimer polypeptides that are preferred locations for mutagenesis is called "alanine scanning mutagenesis," as described by Cunningham and Wells, *Science*, 244:1081-1085 (1989). Here, a residue or group of target residues are identified (e.g. charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined.

Normally the mutations will involve conservative amino acid replacements in non-functional regions of the heteromultimer. Exemplary mutations are shown in the following table.

TABLE 3

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Covalent modifications of the heteromultimer polypeptides are included within the scope of this invention. Covalent modifications of the heteromultimer can be introduced into the molecule by reacting targeted amino acid residues of the heteromultimer or fragments thereof with an organic derivatizing agent that is capable of reacting with selected side chains or the N- or C-terminal residues. Another type of covalent modification of the heteromultimer polypeptide included within the scope of this invention comprises altering the native glycosylation pattern of the polypeptide. By altering is meant deleting one or more carbohydrate moieties found in the original heteromultimer, and/or adding one or more glycosylation sites that are not present in the original heteromultimer. Addition of glycosylation sites to the heteromultimer polypeptide is conveniently accomplished by altering the amino acid sequence such that it contains one or more N-linked glycosylation sites. The alteration may also be made by the addition of, or substitution by, one or more serine or threonine residues to the original heteromultimer sequence (for O-linked glycosylation sites). For ease, the heteromultimer amino acid sequence is preferably altered through changes at the DNA level, particularly by mutating the DNA encoding the heteromultimer polypeptide at preselected bases such that codons are generated that will translate into the desired amino acids. Another means of increasing the number of carbohydrate moieties on the heteromultimer polypeptide is by chemical or enzymatic coupling of glycosides to the polypeptide. These methods are described in WO 87/05330 published 11 Sep. 1987, and in Aplin and Wriston, *CRC Crit. Rev. Biochem.*, pp. 259-306 (1981). Removal of carbohydrate moieties present on the heteromultimer may be accomplished chemically or enzymatically.

Another type of covalent modification of heteromultimer comprises linking the heteromultimer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant heteromultimer, it will be appreciated that some screening of the recovered variant will be needed to select the optimal variant.

3. Expression of the Heteromultimer

Following mutation of the DNA as discussed in the preceding section, the DNA encoding the molecule is expressed using recombinant techniques which are widely available in the art. Often, the expression system of choice will involve a mammalian cell expression vector and host so that the heteromultimer is appropriately glycosylated (e.g. in the case of heteromultimers comprising antibody domains which are glycosylated). However, the molecules can also be produced in the prokaryotic expression systems elaborated below. Normally, the host cell will be transformed with DNA encoding both the first polypeptide and the second polypeptide and other polypeptide(s) required to form the heteromultimer, on a single vector or independent vectors. However, it is possible to express the first polypeptide and second polypeptide in independent expression systems and couple the expressed polypeptides in vitro.

The nucleic acid (e.g., cDNA or genomic DNA) encoding the heteromultimer is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The polypeptides of the heteromultimer may be produced as fusion polypeptides with a signal sequence or other polypeptide having a specific cleavage site at the N-terminus of the mature protein or polypeptide. In general, the signal sequence may be a component of the vector, or it may be a part of the DNA that is inserted into the vector. The heterologous signal sequence selected preferably is one that is recognized and processed (i.e., cleaved by a signal peptidase) by the host cell. For prokaryotic host cells, the signal sequence may be substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, alpha factor leader (including *Saccharomyces* and *Kluyveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the antibody or adhesin presequence that normally directs secretion of these molecules from human cells in vivo) is satisfactory, although other mammalian signal sequences may be suitable as well as viral secretory leaders, for example, the herpes simplex gD signal. The DNA for such precursor region is ligated in reading frame to DNA encoding the polypeptides forming the heteromultimer.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors should contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al., *Science* 209:1422 [1980]) or hygromycin (Sugden et al., *Mol. Cell. Biol.* 5:410-413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the heteromultimer nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes heteromultimer. Increased quantities of heteromultimer are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the components of the heteromultimer This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding heteromultimer, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 [1979]; Kingsman et al., *Gene* 7:141 [1979]; or Tschemper et al., *Gene* 10: 157 [1980]). The trp1 gene provides a selection marker for a mutant strain of yeast lacking the ability to grow in tryptophan, for example, ATCC No. 44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Bianchi et al., *Curr. Genet.* 12:185 (1987). More recently, an expression system for large-scale production of recombinant calf chymosin was reported for *K. lactis*. Van den Berg, *Bio/Technology* 8:135 (1990). Stable multi-copy expression vectors for secretion of mature recombinant human serum albumin by industrial strains of *Kluyveromyces* have also been disclosed. Fleer et al., *Bio/Technology* 9:968-975 (1991).

Expression and cloning vectors usually contain a promoter that is recognized by the host organism and is operably linked to the heteromultimer nucleic acid. A large number of promoters recognized by a variety of potential host cells are well known. These promoters are operably linked to heteromultimer-encoding DNA by removing the promoter from the source DNA by restriction enzyme digestion and inserting the isolated promoter sequence into the vector.

Promoters suitable for use with prokaryotic hosts include the β-lactamase and lactose promoter systems (Chang et al., *Nature* 275:615 [1978]; and Goeddel et al., *Nature* 281:544 [1979]), alkaline phosphatase, a tryptophan (trp) promoter system (Goeddel, *Nucleic Acids Res.*, 8:4057 [1980] and EP 36,776) and hybrid promoters such as the tac promoter (de-Boer et al., *Proc. Natl. Acad. Sci. USA* 80:21-25 [1983]). However, other known bacterial promoters are suitable. Their nucleotide sequences have been published, thereby enabling a skilled worker operably to ligate them to DNA encoding the heteromultimer (Siebenlist et al., *Cell* 20:269 [1980]) using linkers or adaptors to supply any required restriction sites. Promoters for use in bacterial systems also will contain a Shine-Dalgarno (S.D.) sequence operably linked to the DNA encoding the heteromultimer.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; and Holland, *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Heteromultimer transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter or from heat-shock promoters.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209: 1422-1427 (1980); Pavlakis et al., *Proc. Natl. Acad. Sci. USA* 78:7398-7402 (1981). The immediate early promoter of the human cytomegalovirus is conveniently obtained as a HindIII E restriction fragment. Greenaway et al., *Gene* 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503-508 (1982) on expressing cDNA encoding immune interferon in monkey cells; Reyes et al., *Nature* 297:598-601 (1982) on expression of human β-interferon cDNA in mouse cells under the control of a thymidine kinase promoter from herpes simplex virus; Canaani and Berg, *Proc. Natl. Acad. Sci. USA* 79:5166-5170 (1982) on expression of the human interferon β1 gene in cultured mouse and rabbit cells; and Gorman et al., *Proc. Natl. Acad. Sci. USA* 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the heteromultimer by higher eukaryotes is often increased by inserting an enhancer sequence into the vector. Enhancers are relatively orientation and position independent, having been found 5' (Laimins et al., *Proc. Natl. Acad. Sci. USA* 78:993 [1981]) and 3' (Lusky et al., *Mol. Cell Bio.* 3:1108 [1983]) to the transcription unit, within an intron (Banerji et al., *Cell* 33:729 [1983]), as well as within the coding sequence itself (Osborne et al., *Mol. Cell Bio.* 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297: 17-18 (1982) on enhancing elements for activation of eukaryotic promoters. The enhancer may be spliced into the vector at a position 5' or 3' to the heteromultimer-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the heteromultimer.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al, *Methods in Enzymology* 65:499 (1980).

Particularly useful in the practice of this invention are expression vectors that provide for the transient expression in mammalian cells of DNA encoding heteromultimer. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of heteromultimers having desired binding specificities/affinities.

Other methods, vectors, and host cells suitable for adaptation to the synthesis of the heteromultimer in recombinant vertebrate cell culture are described in Gething et al., *Nature* 293:620-625 (1981); Mantei et al., *Nature* 281:40-46 (1979); Levinson et al.; EP 117,060; and EP 117,058. A particularly useful plasmid for mammalian cell culture expression of the heteromultimer is pRK5 (EP 307,247) or pSVI6B (PCT pub. no. WO 91/08291 published 13 Jun. 1991).

The choice of host cell line for the expression of heteromultimer depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient heteromultimer expression. CDM8-based vectors can be used to transfect COS cells by the DEAE-dextran method (Aruffo et al., *Cell* 61:1303-1313 [1990]; and Zettmeissl et al., *DNA Cell Biol.* (*US*) 9:347-353 [1990]). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture. These clones are grown in the presence of increasing levels of DHFR inhibitor methotrexate and clones are selected in which the number of gene copies encoding the DHFR and heteromultimer sequences is co-amplified. If the immunoadhesin contains a hydrophobic leader sequence at its N-terminus, it is likely to be processed and secreted by the transfected cells. The expression of immunoadhesins with more complex structures may require uniquely suited host cells. For example, components such as light chain or J chain may be provided by certain myeloma or hybridoma host cells (Gascoigne et al., supra; and Martin et al., *J. Virol.* 67:3561-3568 [1993]).

Other suitable host cells for cloning or expressing the vectors herein are prokaryote, yeast, or other higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔptr3 phoAΔE15 Δ(argF-lac)169 ompTΔdegP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed. Alternatively, methods of cloning, e.g., PCR or other nucleic acid polymerase reactions, are suitable.

In addition to prokaryotes, eukaryotic microbes such as filamentous fungi or yeast are suitable cloning or expression hosts for heteromultimer-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature* 290:140 [1981]; EP 139,383 published May 2, 1985); *Kluyveromyces* hosts (U.S. Pat. No. 4,943,529; Peer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; *yarrowia* [EP 402,226]; *Pichia pastoris* (EP 183,070; Sreekrishna et al., *J. Basic Microbiol.* 28:265-278 [1988]); *Candida; Trichoderma reesia* [EP 244,234]; *Neurospora crassa* (Case et al., *Proc. Natl. Acad. Sci. USA* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112:284-289 [1983]; Tilburn et al., *Gene* 26:205-221 [1983]; Yelton et al., *Proc. Natl. Acad. Sci. USA* 81:1470-1474 [1984]) and *A. niger* (Kelly and Hynes, *EMBO J.* 4:475-479 [1985]).

Suitable host cells for the expression of glycosylated heteromultimer are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6:47-55 (1988); Miller et al., in *Genetic Engineering*, Setlow et al., eds., Vol. 8 (Plenum Publishing, 1986), pp. 277-279; and Maeda et al., *Nature* 315:592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the heteromultimer DNA. During incubation of the plant cell culture with *A. tumefaciens*, the DNA encoding the heteromultimer is transferred to the plant cell host such that it is transfected, and will, under appropriate conditions, express the heteromultimer DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

The preferred hosts are vertebrate cells, and propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. USA* 77:4216 [1980]); mouse sertoli cells (TM4, Mather, *Biol. Reprod.* 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 [1982]); MRC 5 cells; FS4 cells; and a human hepatoma line (Hep G2).

Host cells are transfected with the above-described expression or cloning vectors of this invention and cultured in conventional nutrient media modified as appropriate for inducing promoters, selecting transformants, or amplifying the genes encoding the desired sequences. Depending on the host cell used, transfection is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology* 52:456-457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.* 130:946 (1977) and Hsiao et al., *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185:527-537 (1990), and Mansour et al., *Nature* 336:348-352 (1988).

Prokaryotic cells used to produce the heteromultimer polypeptide of this invention are cultured in suitable media as described generally in Sambrook et al., supra.

The mammalian host cells used to produce the heteromultimer of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* 58:44 (1979), Barnes and Sato, *Anal. Biochem.* 102:255 (1980), U.S. Pat. Nos. 4,767,704; 4,657,866; 4,927,762; or 4,560,655; WO 90/03430; WO 87/00195; U.S. Pat. Re. No. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed., IRL Press, 1991.

The host cells referred to in this disclosure encompass cells in culture as well as cells that are within a host animal.

4. Recovery of the Heteromultimer

The heteromultimer preferably is generally recovered from the culture medium as a secreted polypeptide, although it also may be recovered from host cell lysate when directly produced without a secretory signal. If the heteromultimer is membrane-bound, it can be released from the membrane using a suitable detergent solution (e.g. Triton-X 100)

When the heteromultimer is produced in a recombinant cell other than one of human origin, it is completely free of proteins or polypeptides of human origin. However, it is necessary to purify the heteromultimer from recombinant cell proteins or polypeptides to obtain preparations that are substantially homogeneous as to heteromultimer. As a first step, the culture medium or lysate is normally centrifuged to remove particulate cell debris.

Heterodimers having antibody constant domains can be conveniently purified by hydroxylapatite chromatography, gel electrophoresis, dialysis, or affinity chromatography, with affinity chromatography being the preferred purification technique. Where the heteromultimer comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin Sepharose, chromatography on an anion or cation exchange resin (such as a polyaspartic acid column), chromatofocusing, SDS-PAGE, and ammonium sulfate precipitation are also available depending on the polypeptide to be recovered. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.* 62:1-13 [1983]). Protein G is recommended for all mouse isotypes and for human γ3 (Guss et al., *EMBO J.* 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in a heterodimer preparation that is >95% pure.

5. Uses for the Heteromultimer

Many therapeutic applications for the heteromultimer are contemplated. For example, the heteromultimer can be used for redirected cytotoxicity (e.g. to kill tumor cells), as a vaccine adjuvant, for delivering thrombolytic agents to clots, for delivering immunotoxins to tumor cells, for converting enzyme activated prodrugs at a target site (e.g. a tumor), for treating infectious diseases or targeting immune complexes to cell surface receptors.

Therapeutic formulations of the heteromultimer are prepared for storage by mixing the heteromultimer having the desired degree of purity with optional physiologically acceptable carriers, excipients, or stabilizers (*Remington's Pharmaceutical Sciences*, 16th edition, Osol, A., Ed., [1980]), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The heteromultimer also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

The heteromultimer to be used for in vivo administration must be sterile. This is readily accomplished by filtration through sterile filtration membranes, prior to or following lyophilization and reconstitution. The heteromultimer ordinarily will be stored in lyophilized form or in solution.

Therapeutic heteromultimer compositions generally are placed into a container having a sterile access port, for example, an intravenous solution bag or vial having a stopper pierceable by a hypodermic injection needle.

The route of heteromultimer administration is in accord with known methods, e.g., injection or infusion by intravenous, intraperitoneal, intracerebral, intramuscular, intraocular, intraarterial, or intralesional routes, or by sustained release systems as noted below. The heteromultimer is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.* 15:167-277 (1981) and Langer, *Chem. Tech.* 12:98-105 (1982) or poly(vinylalcohol)], polylactides (U.S. Pat. No. 3,773,919, EP 58,481), copolymers of L-glutamic acid and gamma ethyl-L-glutamate (Sidman et al., *Biopolymers* 22:547-556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release heteromultimer compositions also include liposomally entrapped heteromultimer. Liposomes containing heteromultimer are prepared by methods known per se: DE 3,218,121; Epstein et al., *Proc. Natl. Acad. Sci. USA* 82:3688-3692 (1985), Hwang et al., *Proc. Natl. Acad. Sci. USA* 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal heteromultimer therapy.

An effective amount of heteromultimer to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 10 mg/kg or more, depending on the factors mentioned above. Typically, the clinician will administer heteromultimer until a dosage is reached that achieves the desired effect. The progress of this therapy is easily monitored by conventional assays.

The heteromultimers described herein can also be used in enzyme immunoassays. To achieve this, one arm of the heteromultimer can be designed to bind to a specific epitope on the enzyme so that binding does not cause enzyme inhibition, the other arm of the heteromultimer can be designed to bind to the immobilizing matrix ensuring a high enzyme density at the desired site. Examples of such diagnostic heteromultimers include those having specificity for IgG as well as ferritin, and those having binding specificities for horse radish peroxidase (HRP) as well as a hormone, for example.

The heteromultimers can be designed for use in two-site immunoassays. For example, two bispecific heteromultimers are produced binding to two separate epitopes on the analyte protein—one heteromultimer binds the complex to an insoluble matrix, the other binds an indicator enzyme.

Heteromultimers can also be used for in vitro or in vivo immunodiagnosis of various diseases such as cancer. To facilitate this diagnostic use, one arm of the heteromultimer can be designed to bind a tumor associated antigen and the other arm can bind a detectable marker (e.g. a chelator which binds a radionuclide). For example, a heteromultimer having specificities for the tumor associated antigen CEA as well as a bivalent hapten can be used for imaging of colorectal and thyroid carcinomas. Other non-therapeutic, diagnostic uses for the heteromultimer will be apparent to the skilled practitioner.

For diagnostic applications, at least one arm of the heteromultimer typically will be labeled directly or indirectly with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; or an enzyme, such as alkaline phosphatase, beta-galactosidase or horseradish peroxidase (HRP).

Any method known in the art for separately conjugating the heteromultimer to the detectable moiety may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The heteromultimers of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of heteromultimer. The amount of analyte in the test sample is inversely proportional to the amount of standard that becomes bound to the heteromultimer. To facilitate determining the amount of standard that becomes bound, the heteromultimers generally are insolubilized before or after the competition, so that the standard and analyte that are bound to the heteromultimers may conveniently be separated from the standard and analyte which remain unbound.

The heteromultimers are particularly useful for sandwich assays which involve the use of two molecules, each capable of binding to a different immunogenic portion, or epitope, of the sample to be detected. In a sandwich assay, the test sample analyte is bound by a first arm of the heteromultimer which is immobilized on a solid support, and thereafter a second arm of the heteromultimer binds to the analyte, thus forming an insoluble three part complex. See, e.g., U.S. Pat. No. 4,376, 110. The second arm of the heteromultimer may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLES

The $C_H3$ interface between the humanized anti-CD3/CD4-IgG chimera previously described by Chamow et al. *J. Immunol.* 153:4268 (1994) was engineered to maximize the percentage of heteromultimers which could be recovered. Protuberance-into-cavity and wild-type $C_H3$ variants were compared in their ability to direct the formation of a humanized antibody-immunoadhesin chimera (Ab/Ia) anti-CD3/CD4-IgG.

Thus, mutations were constructed in the $C_H3$ domain of the humanized anti-CD3 antibody heavy chain and in CD4-IgG by site-directed mutagenesis using mismatched oligonucleotides (Kunkel et al., *Methods Enzymol.* 154: 367 [1987] and P. Carter, in *Mutagenesis: a Practical Approach*, M. J. McPherson, Ed., IRL Press, Oxford, UK, pp. 1-25 [1991]) and verified by dideoxynucleotide sequencing (Sanger et al., *Proc. Natl. Acad. Sci. USA* 74: 5463 [1977]). See Table 4 below and FIG. 7 herein.

TABLE 4

| $C_H3$ of anti-CD3 | $C_H3$ of CD4-IgG |
|---|---|
| Most Preferred Mutants | |
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| Preferred Mutants | |
| F405W | T394S |

Figure 9:
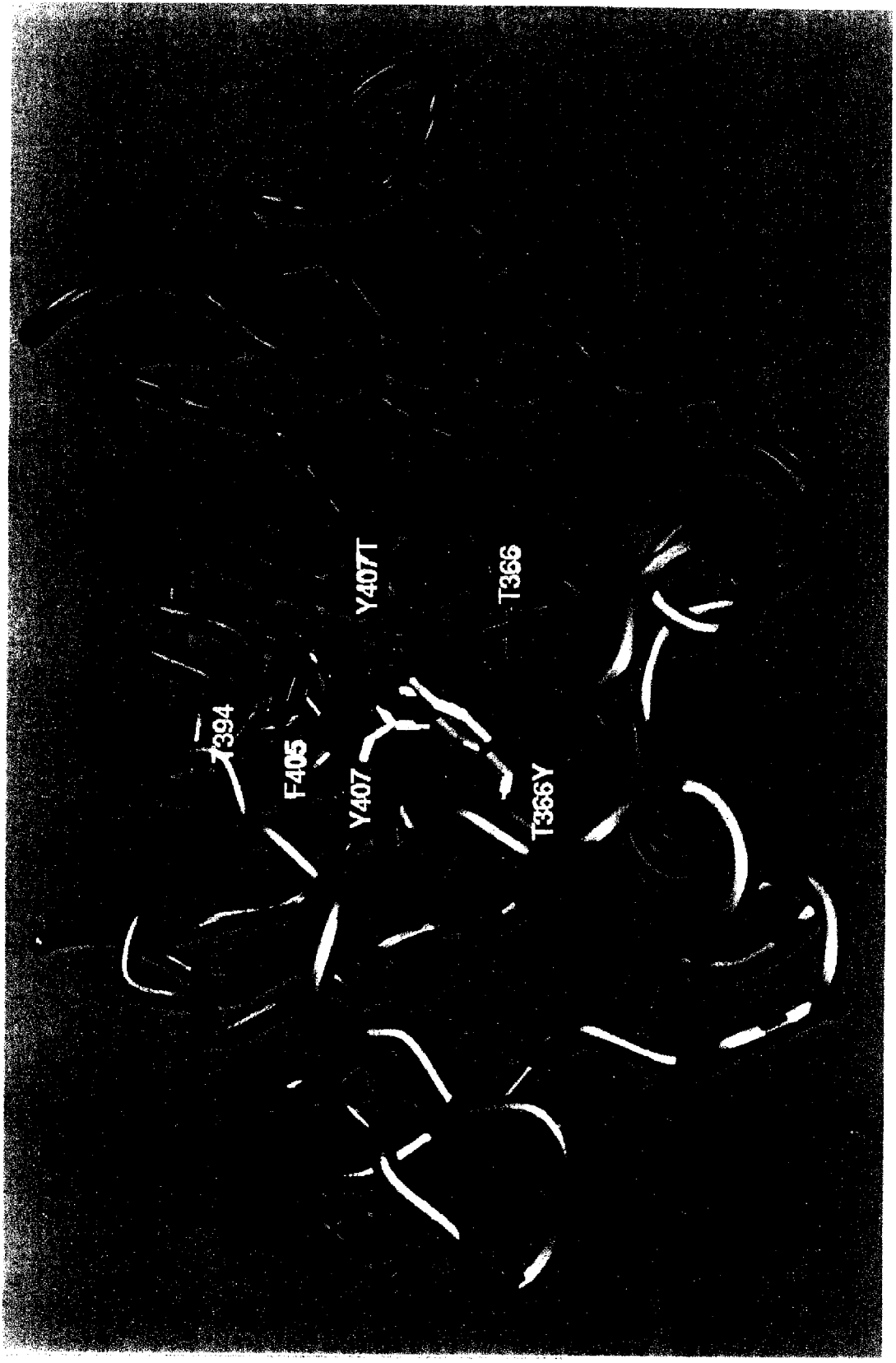
FIG. 9 depicts a C$_H$3 dimer based upon a 2.9 Å structure of human IgG$_1$ Fc (Deisenhofer, *Biochem.* 20:2361 [1981]) highlighting T366Y and Y407T mutations on opposite sides of the interface together with residues Phe$^{405}$ and Thr$^{394}$ ("Kabat numbering"—Kabat et al., *Sequences of Proteins of Immunological Interest*, National Institutes of Health, Bethesda, Md., ed. 5, [1991]).

Residue T366 is within hydrogen-bonding distance of residue Y407 on the partner $C_H3$ domain. Indeed the principal intermolecular contact to residue T366 is to residue Y407 and vice versa. One protuberance-into-cavity pair was created by inverting these residues with the reciprocal mutations of T366Y in one C_H3 domain and Y407T in the partner domain thus maintaining the volume of side chains at the interface (FIG. 9). Mutations are denoted by the wild-type residue followed by the position using the Kabat numbering system (Kabat et al., *Sequences of Proteins of Immunological Interest*, National Institutes of Health, Bethesda, Md., ed. 5, [1991]) and then the replacement residue in single-letter code. Multiple mutations are denoted by listing component single mutations separated by a colon.

Figure 8:
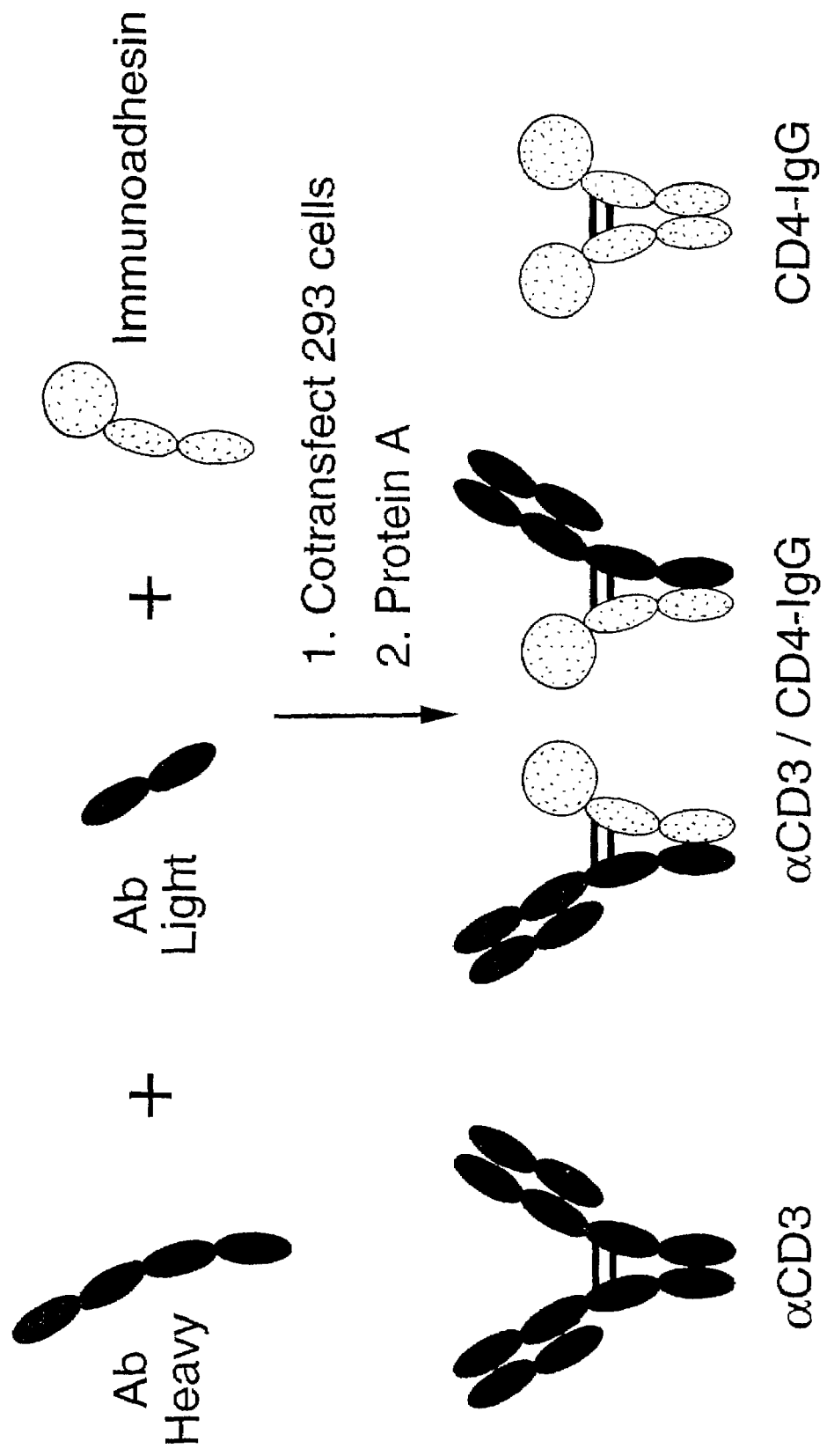
FIG. 8 shows schematically the co-transfection assay for examining Fc heterodimerization described in the examples.

Phagemids encoding anti-CD3 light (L) and heavy (H) chain variants (Shalaby et al., *J. Exp. Med.* 175: 217 [1992] and Rodrigues et al., *Int. J. Cancer (Suppl.)* 7: 45 [1992]) were co-transfected into human embryonic kidney cells, 293S, together with a CD4-IgG variant encoding phagemid (Byrn et al., *Nature* 344: 667 [1990]) as previously described (Chamow et al., *J. Immunol.* 153: 4268 [1994]). The procedure is illustrated in FIG. 8 herein. The total amount of transfected phagemid DNAs was fixed whereas the ratio of different DNAs was varied to maximize the yield of Ab/Ia chimera. The ratio (by mass) of Ia:H chain:L chain input DNAs (15 μg total) was varied as follows: 8:1:3; 7:1:3; 6:1:3; 5:1:3; 4:1:3; 3:1:3; 1:0:0; 0:1:3.

The products were affinity purified using Staphylococcal protein A (ProSep A, BioProcessing Ltd, UK) prior to analysis by SDS-PAGE followed by scanning LASER densitometry (FIGS. 10A-10E). Excess L over H chain DNA was used to avoid the L chain from being limiting. The identity of products was verified by electroblotting on to PVDF membrane (Matsudaira, *J. Biol. Chem.* 262: 10035 [1987]) followed by amino terminal sequencing.

Co-transfection of phagemids for L chain together with those for H chain and Ia incorporating wild-type C_H3 resulted in a mixture of Ab/Ia chimera, IgG and Ia homodimer products as expected (Chamow et al., *J. Immunol.* 153: 4268 [1994]). See FIG. 10A. The larger the fraction of input DNA encoding antibody H plus L chains or Ia the higher the fraction of corresponding homodimers recovered. An input DNA ratio of 6:1:3 of Ia:H:L yielded 54.5% Ab/Ia chimera with similar fractions of Ia homodimer (22.5%) and IgG (23.0%). These ratios are in good agreement with those expected from equimolar expression of each chain followed by random assortment of H chains with no bias being introduced by the method of analysis: 50% Ab/Ia chimera, 25% Ia homodimer and 25% IgG.

TABLE 4

| C_H3 of anti-CD3 | C_H3 of CD4-IgG |
|---|---|
| Most Preferred Mutants | |
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| Preferred Mutants | |
| F405W | T394S |

Figure 10A:
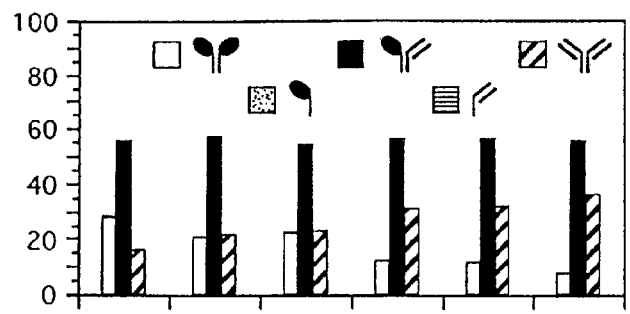
FIGS. 10A-10E depict a scanning densitometric analysis of SDS-PAGE of products from co-transfection of antibody (Ab) heavy (H) and light (L) chains with immunoadhesin (Ia).
Figure 10B:
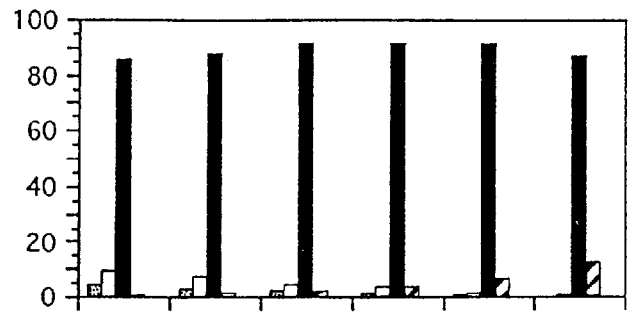
Figure 10C:
Figure 10D:
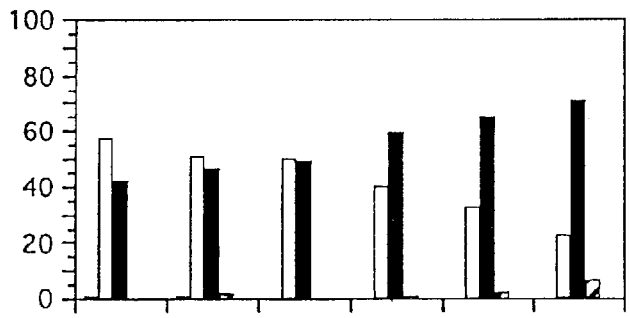
Figure 10E:
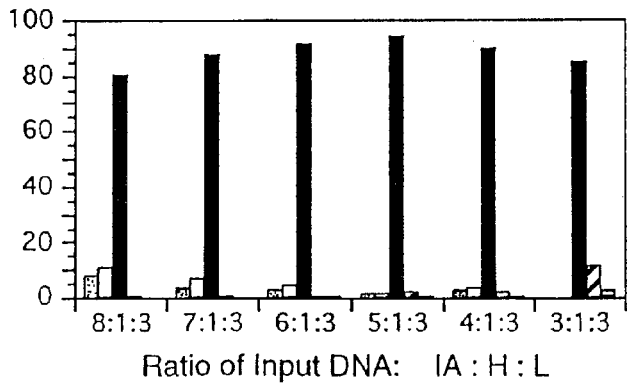

In contrast to chains containing wild-type C_H3, Ab/Ia chimera was recovered in yields of up to 92% from cotransfections in which the anti-CD3 H chain and CD4-IgG Ia contained the Y407T cavity and T366Y protuberance mutations, respectively (FIG. 10B). Similar yields of Ab/Ia chimera were obtained if these reciprocal mutations were installed with the protuberance on the H chain and the cavity in the Ia (FIG. 10C). In both cases monomer was observed for the chain containing the protuberance but not the cavity. Without being limited to any one theory, it is believed that the T366Y protuberance is more disruptive to homodimer formation than the Y407T cavity. The fraction of Ab/Ia hybrid was not significantly changed by increasing the size of both protuberance and cavity (Ab T366W, Ia Y407A). A second protuberance and cavity pair (Ab F405A, Ia T394W) yielded up to 71% Ab/Ia chimera using a small fraction of Ia input DNA to offset the unanticipated proclivity of the Ia T394W protuberance variant to homodimerize (FIG. 10D). Combining the two independent protuberance-into-cavity mutant pairs (Ab T366Y:F405A, Ia T394W:Y407T) did not improve the yield of Ab/Ia hybrid over the Ab T366Y, Ia Y407T pair (compare FIGS. 10C and 10E).

The fraction of Ab/Ia chimera obtained with T366Y and Y407T mutant pair was virtually independent of the ratio of input DNAs over the range tested. Furthermore the contaminating species were readily removed from the Ab/Ia chimera by ion exchange chromatography (0-300 mM NaCl in 20 mM Tris-HCl, pH8.0) on a mono S HR 5/5 column (Pharmacia, Piscataway, N.J.). This augurs well for the preparation of larger quantities Ab/Ia chimeras using stable cell lines where the relative expression levels of Ab and Ia are less readily manipulated than in the transient expression system.

The protuberance-into-cavity mutations identified are anticipated to increase the potential applications of Fc-containing BsAb by reducing the complexity of the mixture of products obtained from a possible ten major species (Suresh et al., *Methods Enzymol.* 121: 210 [1990]) down to four or less. It is expected that the T366Y and Y407T mutant pair will be useful for generating heteromultimers of other human IgG isotypes since T366 and Y407 are fully conserved and other residues at the C_H3 domain interface of IgG_1 are highly conserved (see FIG. 6 herein).

The invention claimed is:

1. A method of preparing a heteromultimer comprising a first polypeptide and a second polypeptide each comprising a $C_H3$ antibody constant domain, wherein said polypeptides meet at an interface, comprising the steps of:
   (a) altering the nucleic acid encoding at least one amino acid residue of the first polypeptide selected from the group consisting of amino acid residues 366, 405, and 407, according to the amino acid numbering as shown in FIG. 5, so as to create a protuberance or cavity; and
   (b) altering the nucleic acid encoding at least one amino acid residue of the second polypeptide selected from the group consisting of amino acid residues 407 if amino acid residue 366 is altered in the first polypeptide, amino acid residue 394 if amino acid residue 405 is altered in the first polypeptide, and amino acid residue 366 if amino acid residue 407 is altered in the first polypeptide, according to the amino acid numbering as shown in FIG. 5, so as to create a cavity or protuberance positionable in a protuberance or cavity, respectively, in the first polypeptide; and
   (c) expressing said nucleic acid in a host cell to obtain the heteromultimer;
   (d) recovering the heteromultimer from the host cell culture.

2. The method of claim 1, wherein the first polypeptide comprises a protuberance and the second polypeptide comprises a cavity.

3. The method of claim 1, wherein said altering the nucleic acid to create a protuberance comprises replacing the nucleic acid encoding the original residue with nucleic acid encoding an import residue having a larger side chain volume than the original residue.

4. The method of claim 3 wherein the import residue is arginine (R).

5. The method of claim 3 wherein the import residue is phenylalanine (F).

6. The method of claim 3 wherein the import residue is tyrosine (Y).

7. The method of claim 3 wherein the import residue is tryptophan (W).

8. The method of claim 1, wherein said altering the nucleic acid to create a cavity comprises replacing the nucleic acid encoding an original residue with nucleic acid encoding an import residue having a smaller side chain volume than the original residue.

9. The method of claim 8 wherein the import residue is not cysteine (C).

10. The method of claim 8 wherein the import residue is alanine (A).

11. The method of claim 8 wherein the import residue is serine (S).

12. The method of claim 8 wherein the import residue is threonine (T).

13. The method of claim 8 wherein the import residue is valine (V).

14. The method of claim 1 wherein the antibody constant domain is from an IgG.

15. The method of claim 1 wherein the heteromultimer is a bispecific antibody.

16. The method of claim 1 wherein the heteromultimer is a bispecific immunoadhesin.

17. The method of claim 1 wherein the heteromultimer is an antibody-immunoadhesin chimera.

18. An isolated heteromultimer prepared by the method of claim 1.

19. An isolated heteromultimer comprising a first polypeptide and a second polypeptide each comprising a $C_H3$ antibody constant domain, wherein (a) the first polypeptide comprises an alteration of at least one amino acid residue selected from the group consisting of amino acid residues 366, 405 and 407, according to the amino acid numbering as shown in FIG. 5, so as to create a protuberance or cavity, and (b) the second polypeptide comprises an alteration of at least one amino acid residue selected from the group consisting of 407 if amino acid residue 366 is altered in the first polypeptide, amino acid residue 394 if amino acid residue 405 is altered in the first polypeptide, and amino acid residue 366 if amino acid residue 407 is altered in the first polypeptide, according to the amino acid numbering as shown in FIG. 5, so as to create a protuberance or cavity positionable in a cavity or protuberance, respectively, in the first polypeptide, and wherein the protuberance or cavity, or both, have been introduced into the interface of the first and second polypeptides respectively.

20. A composition comprising the heteromultimer of claim 19 and a pharmaceutically acceptable carrier.

21. A host cell comprising nucleic acid encoding the heteromultimer of claim 19.

22. The host cell of claim 21 wherein the nucleic acid encoding the first polypeptide and the nucleic acid encoding the second polypeptide are present in a single vector.

23. The host cell of claim 21 wherein the nucleic acid encoding the first polypeptide and the nucleic acid encoding the second polypeptide are present in separate vectors.

24. A method of making a heteromultimer comprising culturing the host cell of claim 21 so that the nucleic acid is expressed and recovering the heteromultimer from the cell culture.

25. The method of claim 24 wherein the host cell is a mammalian cell.

26. The method of claim 24 wherein the heteromultimer is recovered from the cell culture media.

27. The method of claim 1, comprising altering amino acid residue 366 of the first polypeptide and amino acid residue 407 of the second polypeptide.

28. The method of claim 27, wherein said altering creates a protuberance in the first polypeptide and a cavity in the second polypeptide.

29. The method of claim 27, wherein said altering creates a cavity in the first polypeptide and a protuberance in the second polypeptide.

30. The method of claim 1, comprising altering amino acid residue 405 of the first polypeptide and amino acid residue 394 of the second polypeptide.

31. The method of claim 30, wherein said altering creates a protuberance in the first polypeptide and a cavity in the second polypeptide.

32. The method of claim 30, wherein said altering creates a cavity in the first polypeptide and a protuberance in the second polypeptide.

33. The method of claim 1, comprising altering amino acid residue 407 of the first polypeptide and amino acid residue 366 of the second polypeptide.

34. The method of claim 33, wherein said altering creates a protuberance in the first polypeptide and a cavity in the second polypeptide.

35. The method of claim 33, wherein the alteration in the said altering creates a cavity in the first polypeptide and a protuberance in the second polypeptide.

36. The heteromultimer of claim 19, wherein the alteration of the second polypeptide creates a protuberance and alteration of the first polypeptide creates a cavity.

37. The heteromultimer of claim 19, wherein the protuberance comprises the replacement of the original amino acid residue with an import residue with a larger side chain volume.

38. The heteromultimer of claim 37, wherein the import residue is arginine (R).

39. The heteromultimer of claim 37, wherein the import residue is phenylalanine (F).

40. The heteromultimer of claim 37, wherein the import residue is tyrosine (Y).

41. The heteromultimer of claim 37, wherein the import residue is tryptophan (W).

42. The heteromultimer of claim 19, wherein the alteration of the second polypeptide creates a cavity and alteration of the first polypeptide creates a protuberance.

43. The heteromultimer of claim 19, wherein the cavity comprises the replacement of the original amino acid residue with an import residue with a smaller side chain volume.

44. The heteromultimer of claim 43, wherein the import residue is alanine (A).

45. The heteromultimer of claim 43, wherein the import residue is serine (S).

46. The heteromultimer of claim 43, wherein the import residue is threonine (T).

47. The heteromultimer of claim 43, wherein the import residue is valine (V).

48. The heteromultimer of claim 19, wherein the first polypeptide comprises an alteration of amino acid residue 366 and wherein the second polypeptide comprises an alteration of amino acid residue 407.

49. The heteromultimer of claim 19, wherein the first polypeptide comprises an alteration of amino acid residue 405 and wherein the second polypeptide comprises an alteration of amino acid residue 394.

50. The heteromultimer of claim 19, wherein the first polypeptide comprises alterations of amino acid residues 366 and 405 and wherein the second polypeptide comprises alterations of amino acid residues 407 and 394.

51. The heteromultimer of claim 19, wherein the first polypeptide comprises alterations of amino acid residues 405 and 407 and wherein the second polypeptide comprises alterations of amino acid residues 394 and 366.

52. The heteromultimer of claim 19, wherein the first polypeptide comprises an alteration of amino acid residue 407 and wherein the second polypeptide comprises an alteration of amino acid residue 366.

53. The heteromultimer of claim 19, wherein the $C_H3$ domain is from an IgG.

54. The heteromultimer of claim 19, wherein the $C_H3$ domain is from an IgA.

55. The heteromultimer of claim 19, wherein the $C_H3$ domain is from an IgD.

56. The heteromultimer of claim 19, wherein the $C_H3$ domain is from an IgE.

57. The heteromultimer of claim 19, wherein the $C_H3$ domain is from an IgM.

58. The heteromultimer of claim 19, wherein the first or second polypeptide further comprises a binding domain.

59. The heteromultimer of claim 58, wherein the binding domain is an antigen binding domain.

60. The heteromultimer of claim 59, wherein the antigen binding domain is an antibody variable domain.

61. The heteromultimer of claim 58, wherein the binding domain is a ligand binding domain.

62. The heteromultimer of claim 58, wherein the binding domain is a receptor binding domain.

63. The heteromultimer of claim 58, wherein the binding domain is an enzymatic domain.

64. The heteromultimer of claim 19, which is a multispecific antibody.

65. The heteromultimer of claim 64, which is a bi-specific antibody.

66. The heteromultimer of claim 64, which is a tri-specific antibody.

67. The heteromultimer of claim 19, which is an immunoadhesin.

68. The heteromultimer of claim 67, which is multi-specific.

69. The heteromultimer of claim 67, which is a bi-specific.

70. The heteromultimer of claim 19, which is a heterodimer.

71. The heteromultimer of claim 19, which is a heterotrimer.

72. The heteromultimer of claim 19, which is a heterotetramer.

73. The heteromultimer of claim 19, which is an antibody-immunoadhesin.

* * * * *

SEQUENCE LISTING

<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 1

Asp Lys Thr His Thr Cys Pro Pro Cys Pro
1               5                   10

<210> SEQ ID NO 2
<211> LENGTH: 108
<212> TYPE: PRT
<213> ORGANISM: Homo sapiens
<220> FEATURE:
<221> NAME/KEY: MOD_RES
<222> LOCATION: (58)..(58)
<223> OTHER INFORMATION: Val or Met
<220> FEATURE:
<221> NAME/KEY: MOD_RES
<222> LOCATION: (70)..(70)
<223> OTHER INFORMATION: Lys or Arg

<400> SEQUENCE: 2

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Asp Gly Gln Pro
        35                  40                  45

Glu Asn Asn Tyr Lys Thr Thr Pro Pro Xaa Leu Asp Ser Asp Gly Ser
    50                  55                  60

Phe Phe Leu Tyr Ser Xaa Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 3
<211> LENGTH: 113
<212> TYPE: PRT
<213> ORGANISM: Homo sapiens

<400> SEQUENCE: 3

Gly Asn Thr Phe Arg Pro Gln Val His Leu Leu Pro Pro Ser Glu
1               5                   10                  15

Glu Leu Ala Leu Asx Glx Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glx Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys

<210> SEQ ID NO 4
<211> LENGTH: 107
<212> TYPE: PRT
```

<213> ORGANISM: Homo sapiens

<400> SEQUENCE: 4

Gln Ala Pro Val Lys Leu Ser Leu Asn Leu Ala Ser Ser Asp Pro
1               5                   10                  15

Pro Glu Ala Ala Ser Trp Leu Leu Cys Glu Val Ser Gly Phe Ser Pro
            20                  25                  30

Pro Asn Ile Leu Leu Met Trp Leu Glu Asp Gln Arg Glu Val Asn Thr
            35                  40                  45

Ser Gly Phe Ala Pro Ala Arg Pro Pro Gln Pro Gly Ser Thr Thr
        50                  55                  60

Phe Trp Ala Trp Ser Val Leu Arg Val Pro Ala Pro Pro Ser Pro Gln
65                  70                  75                  80

Pro Ala Thr Tyr Thr Cys Val Val Ser His Glu Asp Ser Arg Thr Leu
                85                  90                  95

Leu Asn Ala Ser Arg Ser Leu Glu Val Ser Tyr
            100                 105

<210> SEQ ID NO 5
<211> LENGTH: 110
<212> TYPE: PRT
<213> ORGANISM: Homo sapiens

<400> SEQUENCE: 5

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
            35                  40                  45

Pro Asp Ala Arg His Ser Thr Thr Gln Pro Arg Lys Thr Lys Gly Ser
        50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 6
<211> LENGTH: 106
<212> TYPE: PRT
<213> ORGANISM: Homo sapiens

<400> SEQUENCE: 6

Asp Glx Asx Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asx Ser Val Thr Ile Ser Trp Thr Arg Glx Asp Gly
            35                  40                  45

Glu Ala Val Lys Thr His Thr Asx Ile Ser Glx Ser His Pro Asx Ala
        50                  55                  60

Thr Phe Ser Ala Val Gly Glu Ala Ser Ile Cys Glu Asx Asx Trp Asx
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105

<210> SEQ ID NO 7
<211> LENGTH: 108
<212> TYPE: PRT
<213> ORGANISM: Homo sapiens

<400> SEQUENCE: 7

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asx Gly Glx Pro
        35                  40                  45

Glx Asx Asn Tyr Lys Thr Thr Pro Pro Val Leu Asp Ser Asp Gly Ser
    50                  55                  60

Phe Phe Leu Tyr Ser Lys Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 8
<211> LENGTH: 107
<212> TYPE: PRT
<213> ORGANISM: Homo sapiens

<400> SEQUENCE: 8

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 9
<211> LENGTH: 107
<212> TYPE: PRT
<213> ORGANISM: Homo sapiens

<400> SEQUENCE: 9

Gly Gln Pro Arg Glx Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

```
Asn Asn Tyr Asn Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Ile Phe Ser Cys Ser Val Met His Glu Ala Leu His Asn Arg Phe
                 85                  90                  95

Thr Gln Lys Ser Leu Ser Leu Ser Pro Gly Lys
            100                 105

<210> SEQ ID NO 10
<211> LENGTH: 107
<212> TYPE: PRT
<213> ORGANISM: Homo sapiens

<400> SEQUENCE: 10

Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
                20                  25                  30

Tyr Pro Ser Asp Ile Ala Val Glu Trp Glx Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105

<210> SEQ ID NO 11
<211> LENGTH: 107
<212> TYPE: PRT
<213> ORGANISM: Mus sp.

<400> SEQUENCE: 11

Gly Arg Pro Lys Ala Pro Gln Val Tyr Thr Ile Pro Pro Lys Glu
 1               5                  10                  15

Gln Met Ala Lys Asp Lys Val Ser Leu Thr Cys Met Ile Thr Asp Phe
                20                  25                  30

Phe Pro Glu Asp Ile Thr Val Glu Trp Gln Trp Asx Gly Gln Pro Ala
            35                  40                  45

Glu Asn Tyr Lys Asn Thr Gln Pro Ile Met Asx Thr Asx Gly Ser Tyr
 50                  55                  60

Phe Val Tyr Ser Lys Leu Asn Val Gln Lys Ser Asn Trp Glu Ala Gly
 65                  70                  75                  80

Asn Thr Phe Thr Cys Ser Val Leu His Glu Gly Leu His Asn His His
                 85                  90                  95

Thr Glu Lys Ser Leu Ser His Ser Pro Gly Lys
            100                 105

<210> SEQ ID NO 12
<211> LENGTH: 107
<212> TYPE: PRT
<213> ORGANISM: Mus sp.

<400> SEQUENCE: 12

Gly Pro Val Arg Ala Pro Gln Val Tyr Val Leu Pro Pro Pro Ala Glu
```

```
                    1               5                   10                  15
Glu Met Thr Lys Lys Glx Phe Ser Leu Thr Cys Met Ile Thr Gly Phe
                    20                  25                  30
Leu Pro Ala Glu Ile Ala Val Glu Trp Thr Ser Asn Gly Arg Thr Glu
                    35                  40                  45
Gln Asn Tyr Lys Asn Thr Ala Thr Val Leu Asp Ser Asp Gly Ser Tyr
                    50                  55                  60
Phe Met Tyr Ser Lys Leu Arg Val Glx Lys Ser Thr Trp Glu Arg Gly
65                      70                  75                  80
Ser Leu Phe Ala Cys Ser Val Val His Glu Gly Leu His Asn His Leu
                    85                  90                  95
Thr Thr Lys Thr Phe Ser Arg Ser Leu Gly Lys
                    100                 105

<210> SEQ ID NO 13
<211> LENGTH: 107
<212> TYPE: PRT
<213> ORGANISM: Mus sp.

<400> SEQUENCE: 13

Gly Leu Val Arg Ala Pro Gln Val Tyr Thr Leu Pro Pro Ala Glu
1                   5                   10                  15
Gln Leu Ser Arg Lys Asp Val Ser Leu Thr Cys Leu Val Val Gly Phe
                    20                  25                  30
Asn Pro Gly Asp Ile Ser Val Glu Trp Thr Ser Asn Gly His Thr Glu
                    35                  40                  45
Glu Asn Tyr Lys Asx Thr Ala Pro Val Leu Asp Ser Asp Gly Ser Tyr
                    50                  55                  60
Phe Ile Tyr Ser Lys Leu Asn Met Lys Thr Ser Lys Trp Glu Lys Thr
65                      70                  75                  80
Asp Ser Phe Ser Cys Asn Val Arg His Glu Gly Leu Lys Asn Tyr Tyr
                    85                  90                  95
Leu Lys Lys Thr Ile Ser Arg Ser Pro Gly Lys
                    100                 105

<210> SEQ ID NO 14
<211> LENGTH: 107
<212> TYPE: PRT
<213> ORGANISM: Mus sp.

<400> SEQUENCE: 14

Gly Arg Ala Gln Thr Pro Gln Val Tyr Thr Ile Pro Pro Pro Arg Glu
1                   5                   10                  15
Gln Met Ser Lys Lys Lys Val Ser Leu Thr Cys Leu Val Thr Asn Phe
                    20                  25                  30
Phe Ser Glu Ala Ile Ser Val Glu Trp Glu Arg Asn Gly Glu Leu Glu
                    35                  40                  45
Gln Asp Tyr Lys Asn Thr Pro Pro Ile Leu Asp Ser Asp Gly Thr Tyr
                    50                  55                  60
Phe Leu Tyr Ser Lys Leu Thr Val Asp Thr Asp Ser Trp Leu Gln Gly
65                      70                  75                  80
Glu Ile Phe Thr Cys Ser Val Val His Glu Ala Leu His Asn His His
                    85                  90                  95
Thr Gln Lys Asn Leu Ser Arg Ser Pro Gly Lys
                    100                 105
```

```
<210> SEQ ID NO 15
<211> LENGTH: 29
<212> TYPE: PRT
<213> ORGANISM: Homo sapiens

<400> SEQUENCE: 15

Lys Asp Glu Phe Ile Cys Arg Ala Val His Glu Ala Ala Ser Pro Ser
1               5                   10                  15

Gln Thr Val Gln Arg Ala Val Ser Val Asn Pro Gly Lys
            20                  25

<210> SEQ ID NO 16
<211> LENGTH: 5
<212> TYPE: PRT
<213> ORGANISM: Homo sapiens

<400> SEQUENCE: 16

Gln Val Tyr Thr Leu
1               5

<210> SEQ ID NO 17
<211> LENGTH: 11
<212> TYPE: PRT
<213> ORGANISM: Homo sapiens

<400> SEQUENCE: 17

Val Ser Leu Thr Cys Leu Val Lys Gly Phe Tyr
1               5                   10

<210> SEQ ID NO 18
<211> LENGTH: 11
<212> TYPE: PRT
<213> ORGANISM: Homo sapiens

<400> SEQUENCE: 18

Gly Ser Phe Phe Leu Tyr Ser Lys Leu Thr Val
1               5                   10

<210> SEQ ID NO 19
<211> LENGTH: 8
<212> TYPE: PRT
<213> ORGANISM: Homo sapiens

<400> SEQUENCE: 19

Lys Thr Thr Pro Pro Val Leu Asp
1               5
```